(12) United States Patent
Teles et al.

(10) Patent No.: US 9,688,648 B2
(45) Date of Patent: Jun. 27, 2017

(54) PROCESS FOR THE PREPARATION OF PROPYLENE OXIDE

(71) Applicants: BASF SE, Ludwigshafen (DE); DOW GLOBAL TECHNOLOGIES LLC, Midland, MI (US)

(72) Inventors: Joaquim Henrique Teles, Waldsee (DE); Bianca Seelig, Cologne (DE); Dominic Riedel, Mannheim (DE); Philip Kampe, Singapore (SG); Daniel Urbanczyk, Griesheim (DE); Markus Weber, Limburgerhof (DE); Ulrich Mueller, Neustadt (DE); Andrei-Nicolae Parvulescu, Heidelberg (DE); Alexander Schroeder, Wattenheim (DE); Meinolf Weidenbach, Stade (DE); Werner Witzl, Stade (DE)

(73) Assignees: BASF SE, Ludwigshafen (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/906,852

(22) PCT Filed: Jul. 16, 2014

(86) PCT No.: PCT/EP2014/065249
§ 371 (c)(1),
(2) Date: Jan. 21, 2016

(87) PCT Pub. No.: WO2015/010992
PCT Pub. Date: Jan. 29, 2015

(65) Prior Publication Data
US 2016/0185741 A1  Jun. 30, 2016

(30) Foreign Application Priority Data

Jul. 24, 2013 (EP) .................................... 13177903

(51) Int. Cl.
| | | |
|---|---|---|
| *C07D 301/03* | (2006.01) | |
| *C07D 301/36* | (2006.01) | |
| *B01J 37/10* | (2006.01) | |
| *B01J 29/70* | (2006.01) | |
| *B01J 29/89* | (2006.01) | |
| *B01J 35/00* | (2006.01) | |
| *B01J 37/00* | (2006.01) | |
| *B01J 37/02* | (2006.01) | |
| *C07D 301/12* | (2006.01) | |
| *C07D 303/04* | (2006.01) | |
| *B01J 23/06* | (2006.01) | |
| *B01J 35/02* | (2006.01) | |
| *B01J 27/18* | (2006.01) | |

(52) U.S. Cl.
CPC ............ *C07D 301/36* (2013.01); *B01J 23/06* (2013.01); *B01J 27/18* (2013.01); *B01J 29/7088* (2013.01); *B01J 29/89* (2013.01); *B01J 35/00* (2013.01); *B01J 35/0006* (2013.01); *B01J 35/023* (2013.01); *B01J 35/026* (2013.01); *B01J 37/0009* (2013.01); *B01J 37/0045* (2013.01); *B01J 37/0201* (2013.01); *B01J 37/10* (2013.01); *C07D 301/12* (2013.01); *C07D 303/04* (2013.01); *B01J 2229/186* (2013.01); *B01J 2229/42* (2013.01); *Y02P 20/52* (2015.11)

(58) Field of Classification Search
CPC .. C07D 303/04; C07D 301/36; C07D 301/12; B01J 27/18; B01J 35/0006; B01J 35/026; B01J 35/023; B01J 35/00; B01J 23/06; B01J 29/89; B01J 29/7088; B01J 37/0045; B01J 37/0009; B01J 37/0201; B01J 37/10; B01J 2229/42; B01J 2229/186
USPC ................................................... 549/506, 523
See application file for complete search history.

(56) References Cited

U.S. PATENT DOCUMENTS

| | | |
|---|---|---|
| 5,194,675 A | 3/1993 | Joerg et al. |
| 6,114,551 A | 9/2000 | Levin et al. |
| 7,205,419 B2 | 4/2007 | Strebelle et al. |

(Continued)

FOREIGN PATENT DOCUMENTS

| | | |
|---|---|---|
| EP | 0 427 062 A2 | 5/1991 |
| EP | 1 122 249 A1 | 8/2001 |

(Continued)

OTHER PUBLICATIONS

International Search Report issued Oct. 17, 2014 in PCT/EP2014/065249.

(Continued)

*Primary Examiner* — T. Victor Oh
(74) *Attorney, Agent, or Firm* — Oblon, McClelland, Maier & Neustadt, L.L.P.

(57) ABSTRACT

A continuous process for the preparation of propylene oxide, comprising (i) providing a liquid feed stream comprising propene, hydrogen peroxide, acetonitrile, water, dissolved potassium dihydrogen phosphate, and optionally propane; (ii) passing the liquid feed stream provided in (i) into an epoxidation reactor comprising a catalyst comprising a titanium zeolite of structure type MWW, and subjecting the liquid feed stream to epoxidation reaction conditions; (iii) removing an effluent stream from the epoxidation reactor; wherein the concentration of the dissolved potassium dihydrogen phosphate in the liquid feed stream is at least 10% of the solubility limit of the potassium dihydrogen phosphate in the liquid feed stream.

15 Claims, No Drawings

(56) References Cited

U.S. PATENT DOCUMENTS

| | | |
|---|---|---|
| 2003/0187284 A1 | 10/2003 | Teles et al. |
| 2007/0043226 A1 | 2/2007 | Muller et al. |
| 2012/0142950 A1* | 6/2012 | Teles et al. .......... C07D 301/12 549/531 |
| 2013/0079534 A1 | 3/2013 | Kanazawa |

FOREIGN PATENT DOCUMENTS

| | | | |
|---|---|---|---|
| JP | WO 2012074118 A1 * | 6/2012 | .......... C07D 301/12 |
| WO | WO 2009/008493 A2 | 1/2009 | |
| WO | WO 2011/006990 A1 | 1/2011 | |
| WO | WO 2011/152268 A1 | 12/2011 | |
| WO | WO 2012/074118 A1 | 6/2012 | |
| WO | WO2012157473 | * 11/2012 | |

OTHER PUBLICATIONS

Lihao Tang, et al., "Highly Active Catalysts for the Ring-Opening Polymerization of Ethylene Oxide and Propylene Oxide Based on Products of Alkylaluminum Compounds with Bulky Tetraphenol Ligands" Macromolecules, vol. 41, No. 20, XP055083305, 2008, pp. 7306-7315.
Written Opinion filed Jul. 16, 2014 in PCT/EP2014/065249.
Peng Wu, et al., "Hydrothermal Synthesis of a Novel Titanosilicate with MWW Topology" Chemistry Letters, 2000, pp. 774-775.
"Hydrogen Peroxide" Ullmann's Encyclopedia of Industrial Chemistry, vol. A 13, 1989, pp. 443-466 (with cover page).

* cited by examiner

US 9,688,648 B2

PROCESS FOR THE PREPARATION OF PROPYLENE OXIDE

The present invention relates to a continuous process for the preparation of propylene oxide wherein a titanium zeolite of framework structure type MWW is employed as epoxidation catalyst and wherein in the liquid feed stream passed into the epoxidation reactor, dissolved potassium dihydrogen phosphate is present in a specific concentration.

Propylene oxide is an important intermediate in the chemical industry. A suitable process for the preparation of propylene oxide starts from propene and makes use of hydrogen peroxide as oxidizing agent, acetonitrile as solvent and a heterogeneous zeolitic epoxidation catalyst having MWW framework structure and containing titanium. Reference is made, for example, to WO 2011/006990. Due to its importance for industrial-scale processes, it is desired to carry out this epoxidation reaction as efficiently as possible. Therefore, the conversion rates of the starting materials and the selectivity to propylene oxide should be as high as possible.

For a specific case where hydrogen peroxide is produced in situ in the epoxidation reactor, WO 2009/008493 teaches that an ammonium salt should be present in the reactor. As conceivable salts, ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate and ammonium acetate are disclosed. As preferred salts, ammonium dihydrogen phosphate, ammonium hydrogen phosphate, and ammonium phosphate are mentioned. According to the examples of WO 2009/008493 where hydrogen peroxide is formed in situ from hydrogen and oxygen as starting materials and where, accordingly, a noble metal catalyst is employed in combination with a titanium containing zeolite catalyst of structure type MWW, ammonium dihydrogen phosphate is used. A theoretical example of WO 2009/008493 where hydrogen peroxide is employed as such and where a titanium containing zeolite catalyst of structure type MWW is employed without an additional noble metal catalyst, no ammonium salt is added.

WO 2011/006990, cited above, teaches in the example the use of ammonium dihydrogen phosphate.

It was an object of the present invention to provide an improved continuous process for the epoxidation of propene with hydrogen peroxide as oxidizing agent in the presence of a catalyst containing a titanium zeolite of framework structure type MWW and in the presence of acetonitrile as solvent.

WO 2012/074118 and WO 2011/152268 relate to methods for producing an olefin oxide comprising reacting hydrogen peroxide with an olefin in the presence of a titanosilicate. Both documents disclose that buffers may be added, wherein numerous cations and anions are listed which may serve for forming a buffer. In both documents, ammonium dihydrogen phosphate and diammonium hydrogen phosphate, respectively, are preferred as a buffer.

US 2003/0187284 relates to a method for producing an epoxide, wherein an alkene is reacted with a hydroperoxide in the presence of a zeolite catalyst, and wherein at least one alkali metal salt being fed into the reaction in at least one precursor stream. It is disclosed that dipotassium hydrogen phosphate, disodium hydrogen phosphate, sodium pyrophosphate and sodium acetate are particularly preferred as the at least one alkali metal salt.

Lihao Tang et al., *Macromolecules*, 2008, 41, 7306-7315 discloses catalysts for the ring-opening polymerization of ethylene oxide and propylene oxide based on products of alkylammonium compounds with bulky tetraphenol ligands.

Surprisingly, it was found that this object can be solved if in the continuous reaction, a liquid feed stream to be fed into the epoxidation reactor is provided which comprises propene, hydrogen peroxide, acetonitrile, water, and a specific dissolved potassium salt. In particular, it was found that by increasing the concentration of this potassium salt in the feed stream, the advantageous effects of the epoxidation reaction regarding the high selectivity with respect to propylene oxide and the low selectivities with respect to the by-products and side-products of the epoxidation reaction become even more pronounced.

Therefore, the present invention relates to a continuous process for the preparation of propylene oxide, comprising (i) providing a liquid feed stream comprising propene, hydrogen peroxide, acetonitrile, water, dissolved potassium dihydrogen phosphate, and optionally propane;

(ii) passing the liquid feed stream provided in (i) into an epoxidation reactor comprising a catalyst comprising a titanium zeolite of framework structure type MWW, and subjecting the liquid feed stream to epoxidation reaction conditions in the epoxidation reactor, obtaining a reaction mixture comprising propylene oxide, acetonitrile, water, potassium dihydrogen phosphate, optionally propene, and optionally propane;

(iii) removing an effluent stream from the epoxidation reactor, the effluent stream comprising propylene oxide, acetonitrile, water, at least a portion of the potassium dihydrogen phosphate, optionally propene, and optionally propane;

wherein the concentration of the dissolved potassium dihydrogen phosphate in the liquid feed stream provided in (i) is at least 10% of the solubility limit of the potassium dihydrogen phosphate in the liquid feed stream.

Step (i)

Surprisingly, it was found that the presence of dissolved potassium dihydrogen phosphate ($KH_2PO_4$) in the liquid feed stream provided in (i) allows for a better epoxidation performance of the epoxidation catalyst employed in (ii) which comprises the titanium zeolite of framework structure type MWW, compared to a process as disclosed in the prior art wherein ammonium dihydrogen phosphate was employed.

Further, it was found that if the concentration of the dissolved potassium dihydrogen phosphate in the liquid feed stream provided in (i) is increased from 10% of the solubility limit to higher concentrations, the performance of the epoxidation catalyst employed in (ii) with respect to its selectivity also improves. While it is conceivable that the potassium dihydrogen phosphate is comprised in the liquid feed stream provided in (i) at a concentration above its solubility limit, it is preferred that said concentration is at most 100% of the solubility limit in order to avoid the presence of non-dissolved potassium dihydrogen phosphate salt in the feed stream. Therefore, the present invention also relates to the process as described above, wherein the concentration of the dissolved potassium dihydrogen phosphate in the liquid feed stream provided in (i) is preferably in the range of from 10 to 100%, more preferably from 15 to 100%, more preferably from 20 to 100%, more preferably from 25 to 100%, more preferably from 30 to 100%, more preferably from 35 to 100%, more preferably from 40 to 100% of the solubility limit of the potassium dihydrogen phosphate in the liquid feed stream provided in (i). Preferred ranges are, for example, from 50 to 100% or from 60 to 100% or from 70 to 100% or from 80 to 100%. Therefore, the present invention also relates to the process as described above, wherein the concentration of the dissolved potassium dihydrogen phosphate in the liquid feed stream provided in (i) is preferably in the range of from 50 to 100%, more preferably from 60 to 100%, more preferably from 70 to 100%, more preferably from 80 to 100% of the solubility limit of the potassium dihydrogen phosphate in the liquid feed stream provided in (i).

The term "solubility limit of the potassium dihydrogen phosphate in the liquid feed stream" as used in the context of the present invention relates to the saturation concentration of the potassium dihydrogen phosphate in the liquid feed stream, where by adding more potassium dihydrogen phosphate, the concentration of the potassium dihydrogen phosphate as solute in the liquid feed stream does not increase and the potassium dihydrogen phosphate would begin to precipitate. The solubility limit of the potassium dihydrogen phosphate in the liquid feed stream will depend on the composition of the liquid feed stream and the conditions such as the temperature at which, and the pressure under which, the liquid feed stream is provided in (i). Determining the solubility limit of potassium dihydrogen phosphate in the liquid feed stream is an easy and straightforward task for the skilled person knowing said conditions and said composition of a given liquid feed stream. A simple procedure to evaluate whether the amount of potassium dihydrogen phosphate being added is above the solubility limit is passing the liquid feed stream before entering the epoxidation reactor through a filter and measure the pressure drop across the filter. If the pressure drop across the filter increases with time on stream and potassium dihydrogen phosphate is found on the filter when it is taken offline, the amount of potassium dihydrogen phosphate being added is already above the solubility limit.

Generally, the molar ratio of water relative to acetonitrile in the liquid feed stream provided in (i) is not subject to any specific restrictions. Preferably, said molar ratio may have any value resulting from the respective preferred concentrations of water and acetonitrile as described above. More preferably, in the liquid feed stream provided in (i), passed into the epoxidation reactor and subjected to epoxidation reactor in (ii), the molar ratio of water relative to acetonitrile is at most 1:4, more preferably in the range of from 1:50 to 1:4, preferably from 1:15 to 1:4.1, more preferably from 1:10 to 1:4.2.

Preferably, the liquid feed stream provided in (i) comprises
the acetonitrile in amount of from 60 to 75 weight-%, preferably from 60 to 65 weight-%, based on the total weight of the liquid feed stream;
the hydrogen peroxide in an amount of from 6 to 10 weight-%, preferably from 7 to 9 weight-%, based on the total weight of the liquid feed stream;
the water in a molar ratio of water relative to acetonitrile of at most 1:4, preferably in the range of from 1:50 to 1:4, preferably from 1:15 to 1:4, more preferably from 1:10 to 1:4.2;
the propene with a molar ratio of propene relative to hydrogen peroxide comprised in the liquid feed stream in the range of from 1:1 to 1.5:1, preferably from 1.1:1 to 1.4:1;
the dissolved potassium dihydrogen phosphate with a molar ratio of potassium dihydrogen phosphate relative to hydrogen peroxide comprised in the liquid feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1; and
optionally the propane with a molar ratio of propane relative to the sum of propene and propane in the range of from 0.0001:1 to 0.15:1, preferably from 0.001:1 to 0.05:1.

Preferably, at least 95 weight-%, preferably from 95 to 100 weight-%, more preferably from 96 to 100 weight-%, more preferably from 97 to 100 weight-%, more preferably from 98 to 100 weight-% of the liquid feed stream provided in (i) consist of propene, hydrogen peroxide, acetonitrile, water, dissolved potassium dihydrogen phosphate, and optionally propane.

Preferably, the liquid feed stream provided in (i), preferably passed as the sole feed stream into the epoxidation reactor, contains potassium with a molar ratio of potassium relative to hydrogen peroxide comprised in the liquid feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1.

Further preferably, the molar ratio of potassium dihydrogen phosphate relative to hydrogen peroxide comprised in the liquid feed stream is above $160 \times 10^{-6}$:1, preferably in the range of from $260 \times 10^{-6}$:1 to $1000 \times 10^{-6}$:1, more preferably from $300 \times 10^{-6}$:1 to $1000 \times 10^{-6}$:1, more preferably from $400 \times 10^{-6}$:1 to $1000 \times 10^{-6}$:1, more preferably from $500 \times 10^{-6}$:1 to $1000 \times 10^{-6}$:1. Further preferably, the molar ratio of potassium dihydrogen phosphate relative to hydrogen peroxide comprised in the liquid feed stream is in the range of from $500 \times 10^{-6}$:1 to $1000 \times 10^{-6}$:1, more preferably from $500 \times 10^{-6}$:1 to $975 \times 10^{-6}$:1, more preferably from $500 \times 10^{-6}$:1 to $950 \times 10^{-6}$:1.

Preferably, the liquid feed stream provided in (i), preferably passed as the sole feed stream into the epoxidation reactor, contains potassium with a molar ratio of potassium relative to hydrogen peroxide comprised in the liquid feed stream of more than $160 \times 10^{-6}$:1, preferably in the range of from $260 \times 10^{-6}$:1 to $1000 \times 10^{-6}$:1, more preferably from $300 \times 10^{-6}$:1 to $1000 \times 10^{-6}$:1, more preferably from $400 \times 10^{-6}$:1 to $1000 \times 10^{-6}$:1, more preferably from $500 \times 10^{-6}$:1 to $1000 \times 10^{-6}$:1. Further preferably, the molar ratio of potassium relative to hydrogen peroxide comprised in the liquid feed stream is in the range of from $500 \times 10^{-6}$:1 to $1000 \times 10^{-6}$:1, more preferably from $500 \times 10^{-6}$:1 to $975 \times 10^{-6}$:1, more preferably from $500 \times 10^{-6}$:1 to $950 \times 10^{-6}$:1.

Therefore, the liquid feed stream provided in (i) preferably comprises
the acetonitrile in amount of from 60 to 75 weight-%, preferably from 60 to 65 weight-%, based on the total weight of the liquid feed stream;
the hydrogen peroxide in an amount of from 6 to 10 weight-%, preferably from 7 to 9 weight-%, based on the total weight of the liquid feed stream;
the water in a molar ratio of water relative to acetonitrile of at most 1:4, preferably in the range of from 1:50 to 1:4, preferably from 1:15 to 1:4, more preferably from 1:10 to 1:4.2;
the propene with a molar ratio of propene relative to hydrogen peroxide comprised in the liquid feed stream in the range of from 1:1 to 1.5:1, preferably from 1.1:1 to 1.4:1;
the dissolved potassium dihydrogen phosphate with a molar ratio of potassium dihydrogen phosphate relative to hydrogen peroxide comprised in the liquid feed stream in the range of from $500 \times 10^{-6}$:1 to $1000 \times 10^{-6}$:1, more preferably from $500 \times 10^{-6}$:1 to $975 \times 10^{-6}$:1, more preferably from $500 \times 10^{-6}$:1 to $950 \times 10^{-6}$:1; and optionally the propane with a molar ratio of propane relative to the sum of propene and propane in the range of from 0.0001:1 to 0.15:1, preferably from 0.001:1 to 0.05:1.

Preferably, the liquid feed stream provided in (i), preferably passed as the sole feed stream into the epoxidation reactor, is free of ammonium dihydrogen phosphate. More preferably, the liquid feed stream provided in (i), preferably passed as the sole feed stream into the epoxidation reactor, is free of ammonium phosphate, ammonium hydrogen phosphate and ammonium dihydrogen phosphate. More preferably, the liquid feed stream provided in (i), preferably passed as the sole feed stream into the epoxidation reactor, is free of ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate, and ammonium acetate. More preferably, the liquid feed stream provided in (i), preferably passed as the sole feed stream into the epoxidation reactor, is free of an ammonium salt. The term "free of" as used in this context of the present invention relates to a concentration of a respective compound of at most 2 weight-ppm, preferably at most 1 weight-ppm, based on the total weight of the liquid feed stream. Therefore, the present invention also relates to the process as described above, wherein the liquid feed stream provided in (i), preferably passed as the sole feed stream into the epoxidation reactor, contains ammonium $NH_4^+$ in amount of at most 2 weight-ppm, preferably at most 1 weight-ppm, based on the total weight of the liquid feed stream.

Preferably, the liquid feed stream provided in (i), preferably passed as the sole feed stream into the epoxidation reactor, contains sodium in a molar ratio of sodium relative to hydrogen peroxide in the range of from $1 \times 10^{-6}$:1 to $250 \times 10^{-6}$:1, preferably from $5 \times 10^{-6}$:1 to $50 \times 10^{-6}$:1.

Preferably, the liquid feed stream provided in (i), preferably passed as the sole feed stream into the epoxidation reactor, does not comprise dissolved dipotassium hydrogenphosphate ($K_2HPO_4$).

Generally, the liquid feed stream can be provided in (i) according to any conceivable method. Preferably, the liquid feed stream is provided in (i) by combining at least four individual streams wherein a first stream comprises hydrogen peroxide, a second stream comprises propene and optionally propane, a third stream comprises acetonitrile and optionally water, and a fourth stream comprises potassium dihydrogen phosphate in an amount so that the concentration of the dissolved potassium dihydrogen phosphate in the liquid feed stream provided in (i) and resulting from combining the at least four individual streams is at least 10%, preferably in the range of from 10 to 100%, more preferably from 15 to 100%, more preferably from 20 to 100%, more preferably from 25 to 100%, more preferably from 30 to 100%, more preferably from 35 to 100%, more preferably from 40 to 100%, more preferably from 50 to 100%, more preferably from 60 to 100%, more preferably from 70 to 100%, more preferably from 80 to 100% of the solubility limit of the potassium dihydrogen phosphate in the liquid feed stream provided in (i).

These at least four individual stream can be combined in every suitably order. Preferably, the stream comprising potassium dihydrogen phosphate is combined with the stream comprising hydrogen peroxide, and the resulting combined stream is combined with a stream which results from combining the stream comprising acetonitrile and the stream comprising propene and optionally propane. The thus obtained stream is the liquid stream provided in (i).

Therefore, the present invention also relates to the process as described above, wherein in (i), the liquid feed stream is provided by combining a stream comprising hydrogen peroxide, a stream comprising acetonitrile and optionally water, and a stream comprising propene and optionally propane, wherein an aqueous stream comprising the dissolved potassium dihydrogen phosphate is combined with the stream comprising hydrogen peroxide, or with the stream comprising acetonitrile and optionally water, or with the stream comprising propene and optionally propane, or with a mixed stream of two or three of these streams, preferably with the stream comprising hydrogen peroxide.

Preferably, the stream comprising potassium dihydrogen phosphate is an aqueous stream of potassium dihydrogen phosphate wherein preferably at least 98 weight-%, more preferably at least 99 weight-%, more preferably at least 99.5 weight-%, more preferably at least 99.9 weight-% of the aqueous stream consist of water and potassium dihydrogen phosphate. Preferably, the aqueous stream contains the potassium dihydrogen phosphate in a concentration in the range of from 0.1 to 18 weight-%, more preferably from 0.2 to 15 weight-%, more preferably from 0.5 to 10 weight-%, more preferably from 1 to 5 weight-%, more preferably from 1 to 3 weight-%, based on the total weight of the stream.

Preferably, the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

Preferably, the stream comprising propene and optionally propene is free of potassium cations ($K^+$) and free of phosphorus (P) in the form of anions of at least one phosphorus oxyacid. The term "free of potassium cations ($K^+$)" as used in this context of the present invention refers to a stream comprising propene and optionally propane, containing potassium cations ($K^+$) in an amount of less than 1 weight-ppm, preferably less than 0.1 weight-ppm, based on the total weight of the stream. The term "free of phosphorus (P) in the form of anions of at least one phosphorus oxyacid" as used in this context of the present invention refers to a stream comprising propene and optionally propane, containing phosphorus (P) in the form of anions of at least one phosphorus oxyacid in an amount of less than 1 weight-ppm, preferably less than 0.1 weight-ppm, based on the total weight of the stream.

According to the process of the present invention, it is conceivable that in addition to the stream comprising propene and optionally propane which is used for providing the liquid feed stream in (i), a further stream comprising propene and optionally propane may be employed. This further stream is preferably formed in step (iv) of the present invention described hereinbelow, wherein the epoxidation mixture removed according to (iii) is subjected to distillation. In step (iv), in addition to the bottoms stream comprising propylene oxide, acetonitrile and water and being depleted of propene and optionally propane, a distillation top stream is obtained being enriched in propene and optionally propane. This top stream, optionally after work-up, can be recycled to the epoxidation reaction as part of the liquid feed stream provided in (i). The volume ratio of the fresh stream comprising propene and optionally propane relative to the recycled stream comprising propene and optionally propane is in the range of from 0.1:1 to 20:1, preferably from 1:1 to 10:1, more preferably from 2:1 to 5:1.

Preferably, in the continuous process of the present invention, the stream comprising acetonitrile which is used for providing the liquid feed stream in (i) at least partially, preferably essentially consists of a recycled acetonitrile stream resulting from the work-up of the effluent stream which is removed in (iii) from the epoxidation reactor and which comprises propylene oxide, acetonitrile, water, potassium dihydrogen phosphate, optionally propene, and optionally propane. During the work-up of the effluent stream, it is preferred to remove essentially all compounds other than acetonitrile and water from the stream and recycle the thus purified stream back to the epoxidation reaction. According to a preferred work-up of the present invention, the stream comprising propene and optionally propane as described above is combined with the acetonitrile recycle stream, either after the final purification stage of the acetonitrile recycle stream or before the final purification stage or final purification stages of the acetonitrile recycle stream. Preferably, the stream comprising propene and optionally propane as described above is combined with the acetonitrile recycle stream before the final purification stages, more preferably before a work-up stage where a stream comprising acetonitrile and water is subjected to a phase separation, preferably a liquid-liquid phase separation and where this phase separation is carried out using the stream comprising propene and optionally propane as separation-promoting compound. Optionally, after this separation stage, the resulting acetonitrile recycle stream, now additionally containing propene and optionally propane, can be subjected to further purification. An especially preferred work-up of the effluent stream removed according to step (iii) is described in detail hereinbelow. Preferably, the acetonitrile recycle stream to which the stream comprising propene and optionally comprising propane had been added and which had been preferably subjected to phase separation and optional further purification has a composition of which preferably at least 98 weight-%, more preferably at least 99 weight-%, more preferably at least 99.5 weight-% consist of acetonitrile, water, and propene. More preferably, at least 75 weight-%, more preferably in the range of from 75 to 90 weight-%, more preferably from 80 to 85 weight-% of the recycle stream consist of acetonitrile and water. In the recycle stream, the molar ratio of acetonitrile relative to water is preferably at most 1:9, more preferably in the range of from 1:50 to 1:9, preferably from 1:25 to 1:9, more preferably from 1:25 to 1:10. A preferred process for working up the effluent stream and recycling the acetonitrile is described hereinbelow.

For starting the continuous process of the present invention and for compensating any losses of acetonitrile in the course of the work-up of the effluent stream obtained in (iii), a part of the stream comprising acetonitrile used for providing the liquid feed stream in (i) can be a make-up acetonitrile stream. Preferably, the make-up acetonitrile stream is a chemical grade acetonitrile stream having an acetonitrile content of preferably at least 99.5 weight-%, more preferably at least 99.7 weight-%, more preferably at least 99.8 weight-%. Preferably, during the continuous process of the present invention, the weight ratio of the recycled acetonitrile stream relative to the make-up acetonitrile stream is in the range of from 1000:1 to 100:1, preferably from 950:1 to 300:1, more preferably from 900:1 to 500:1.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight % or from 35 to 75 weight-% or from 40 to 70 weight-%.

According to the present, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, $5^{th}$ edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/reoxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1\times10^{-6}:1$ to $250\times10^{-6}:1$, more preferably from $5\times10^{-6}:1$ to $50\times10^{-6}:1$.

The temperature and the pressure of the liquid feed stream which is passed into the reactor in (ii) are not subject to any specific restrictions provided that the stream is liquid. It is possible that the liquid feed stream fed into the reactor in (ii) consists of one single liquid phase, of two liquid phases, or of three or more liquid phases. Preferably, the liquid feed stream fed into the reactor in (ii) consists of one single liquid phase or of two liquid phases, more preferably of one single liquid phase.

Preferably, the liquid feed stream passed into the reactor in (ii) has a temperature in the range of from 0 to 60° C., more preferably from 10 to 55° C., more preferably from 25 to 50° C.

Preferably, the liquid feed stream passed into the reactor in (ii) is at a pressure in the range of from 14 to 100 bar, more preferably from 14.5 to 50 bar, more preferably from 15 to 25 bar. Therefore, the present invention relates to the process as described above, wherein the liquid feed stream passed into the reactor in (ii) has a temperature in the range of from 0 to 60° C., preferably from 25 to 50° C., and is at a pressure in the range of from 14 to 100 bar, preferably from 15 to 25 bar.

Step (ii)
The Catalyst Comprising a Titanium Zeolite of Framework Structure Type MWW According to step (ii) of the process of the present invention, the liquid feed stream provided in (i) is passed into an epoxidation reactor comprising a catalyst comprising a titanium zeolite of framework structure type MWW. The term "titanium zeolite of framework structure type MWW" as used in the context of the present invention, also referred to as "TiMWW", relates to a zeolite of framework structure MWW which contains titanium as isomorphous substitution element in the zeolitic framework. Preferably, the zeolitic framework is essentially free of aluminum and essentially consists of silicon, titanium, and oxygen. Preferably, at least 99 weight-%, more preferably at least 99.5 weight-%, more preferably at least 99.9 weight-% of the zeolitic framework consist of silicon, titanium, and oxygen. Optionally, the titanium zeolite of framework structure type MWW may comprise extra-framework titanium which is to be understood as every titanium species which is not part of the MWW zeolitic framework. The preparation of TiMWW catalysts is described, for example, in US 2007043226 A1, in particular in Examples 3 and 5 of US 2007043226 A1.

The titanium content of the titanium zeolite of framework structure type MWW is not subject to any specific restrictions. Preferably, the titanium zeolite of framework structure type MWW comprised in the catalyst in (ii) contains titanium, calculated as elemental titanium, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (ii) contains titanium, calculated as elemental titanium, in an amount in the range of from 0.1 to 5 weight-%, preferably from 1 to 2 weight-%, silicon, based on the total weight of the titanium zeolite of framework structure type MWW.

In addition to the titanium, the titanium zeolite of framework structure type MWW may comprise at least one further element other than titanium, silicon, and oxygen. Generally, it is conceivable that this at least one further element is an isomorphous substitution element which is part of the MWW zeolitic framework structure. Preferably, this at least one further element is not an isomorphous substitution element. Such a further element which is not an isomorphous substitution element can be applied to the zeolite by, for example, a spray process, a wet impregnation process such as an incipient wetness process, or any other suitable process. Preferably, the at least one further element is selected from the group consisting of Al, Zr, V, Nb, Ta, Cr, Mo, W, Mn, Fe, Co, Ni, Zn, Ga, Ge, In, Sn, Pb, and a combination of two or more, preferably from the group consisting of Zr, V, Nb, Ta, Cr, Mo, W, Mn, Fe, Co, Ni, Zn, Ga, Ge, In, Sn, Pb, and a combination of two or more. More preferably, the titanium zeolite of framework structure type MWW contains zinc as further element in addition to titanium, silicon, and oxygen. More preferably, the titanium zeolite of framework structure type MWW contains zinc as the sole further element in addition to titanium, silicon, and oxygen. More preferably, the titanium zeolite of framework structure type MWW contains zinc as the sole further element in addition to titanium, silicon, and oxygen wherein at least 99 weight-%, more preferably at least 99.5 weight-%, more preferably at least 99.9 weight-% of the zeolitic framework structure consist of silicon, titanium, and oxygen. More preferably, in case the titanium zeolite of framework structure type MWW contains zinc as the sole further element, at least 99 weight-%, more preferably at least 99.5 weight-%, more preferably at least 99.9 weight-% of the titanium zeolite of framework structure type MWW consist of zinc, titanium, silicon, and oxygen; this titanium zeolite of framework structure type MWW which contains zinc as the sole further element is also referred to as "ZnTiMWW".

The zinc content of the titanium zeolite of framework structure type MWW is not subject to any specific restrictions. Preferably, the titanium zeolite of framework structure type MWW comprised in the catalyst in (ii) contains zinc, calculated as elemental zinc, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (ii) contains zinc, calculated as elemental zinc, in an amount in the range of from 0.1 to 5 weight-%, preferably from 1 to 2 weight-%, based on the total weight of the titanium zeolite of framework structure type MWW.

The catalyst according to (ii), comprising the titanium zeolite of framework structure type MWW, can consist of the titanium zeolite of framework structure type MWW, preferably consist of the TiMWW or the ZnTiMWW as described. In such cases, the catalyst can be the titanium zeolite of framework structure type MWW in the form of the zeolitic powder which can be molded, for example as a granules, a microsphere such as a microsphere obtained from spray drying or by a spray granulation, a shaped body having, for example, the shape of a pellet, a tablet, a cylinder, a wheel, a star, a sphere, and so forth.

Preferably, the catalyst according to (ii), comprising the titanium zeolite of framework structure type MWW, preferably the TiMWW or the ZnTiMWW, is prepared as a molding comprising the titanium zeolite of framework structure type MWW, preferably the TiMWW or the ZnTiMWW, by suitably mixing the titanium zeolite of framework structure type MWW with at least one binder and/or with at least one binder precursor, and optionally at least one pore-forming agent and/or at least one plasticizing agent. The moldings may be shaped in every conceivable geometry such as strands, for example having rectangular, triangular hexagonal, quadratic, oval, or circular cross-section, stars, tablets, spheres, hollow cylinders, and the like. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg, with $SiO_2$ being preferred. Pore-forming agent such as mesopore-forming agents include polymeric vinyl compounds, such as polyalkylene oxides like polyethylene oxides, polystyrene, polyacrylates, polymethacrylates, polyolefins, polyamides and polyesters. Pasting agents include organic, in particular hydrophilic polymers, such as carbohydrates like cellulose, cellulose derivatives, such as methyl cellulose, and starch, such as potato starch, wallpaper plaster, polyacrylates, polymethacrylates, polyvinyl alcohol, polyvinyl pyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylene glycol, as pasting agents may be mentioned. Preferably, the catalyst according to (ii), is employed as a molding having the shape of an extrudates, preferably an extrudates having a length of preferably from 1 to 10 mm, more preferably of from 1 to 7 mm, more preferably of from 1 to 5 mm, and a diameter preferably of from 0.1 to 5 mm, more preferably of from 0.2 to 4 mm, more preferably of from 0.5 to 2 mm. In particular as far as the preferred catalyst according to (ii) is concerned comprising the ZnTiMWW, it is preferred to employ this catalyst in the form of a micropowder or in the form of a molding, wherein the molding preferably contains said micropowder.

Said catalyst used according to step (ii) of the present invention in the form of a micropowder, comprising the ZnTiMWW, is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). The Dv10 value is understood as being determined according to Reference Example 4.1 of the present invention.
2. The micropowder of embodiment 1, having a Dv10 value in the range of from 2 to 5.5 micrometer, preferably from 3 to 5.5 micrometer.
3. The micropowder of embodiment 1 or 2, having a Dv50 value in the range of from 7 to 25 micrometer and optionally a Dv90 value in the range of from 26 to 85 micrometer. The Dv50 and Dv90 values are understood as being determined according to Reference Example 4.1 of the present invention.
4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the ZnTiMWW have an average pore diameter in the range of from 1.0 to 1.2 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the ZnTiMWW.
8. The micropowder of any of embodiments 1 to 7, wherein the ZnTiMWW contains zinc in an amount of from 1.0 to 2.0 weight-%, preferably of from 1.2 to 1.9 weight-%, calculated as Zn and based on the weight of the ZnTiMWW.
9. The micropowder of any of embodiments 1 to 8, wherein the ZnTiMWW contains titanium in an amount of from 1.0 to 2.0 weight-%, preferably of from 1.2 to 1.8 weight-%, calculated as Ti and based on the weight of the ZnTiMWW.
10. The micropowder of any of embodiments 1 to 9, having a crystallinity, as determined by X-ray diffraction (XRD) analysis, of at least (80+/−10) %, preferably of at least (85+/−10) %. The crystallinity is understood as being determined according to Reference Example 4.7 of the present invention.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.

12. The micropowder of any of embodiments 1 to 11, comprising, based on the total weight of the micropowder and calculated as element, less than 0.1 weight.-%, preferably less than 0.01 weight-% of boron.
13. The micropowder of any of embodiments 1 to 12, having a bulk density of in the range of from 80 to 100 g/ml.
14. The micropowder of any of embodiments 1 to 13, being a spray powder, preferably obtainable or obtained by spray-drying.

Further, said catalyst used according to step (ii) of the present invention in the form of a molding, comprising the ZnTiMWW, is preferably characterized by the following features and embodiments, including the combinations of embodiments according to the given dependencies:
1. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.
2. The molding of embodiment 1, comprising mesopores having an average pore diameter in the range of from 4 to 40 nm, preferably from 20 to 30 nm as determined by Hg porosimetry according to DIN 66133.
3. The molding of embodiment 1 or 2, having a crystallinity, as determined by XRD analysis, of at least (55+/−10) %, preferably in the range of from ((55 to 75)+/−10) %. The crystallinity is understood as being determined according to Reference Example 4.7 of the present invention.
4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 4.2 of the present invention.
5. The molding of any of embodiments 1 to 4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 4.3 of the present invention.
6. The molding of any of embodiments 1 to 5, the $^{29}$Si-NMR spectrum of said molding comprising six peaks at the following position
    peak 1 at −98+/−x ppm,
    peak 2 at −104+/−x ppm,
    peak 3 at −110+/−x ppm,
    peak 4 at −113+/−x ppm,
    peak 5 at −115+/−x ppm,
    peak 6 at −118+/−x ppm,
with x in any of the peaks being 1.5, preferably 1.0, more preferably 0.5, wherein Q which is defined as $$Q=100*\{[a_1+a_2]/[a_4+a_5+a_6]\}/a_3$$

is at most 2.5, preferably at most 1.6, preferably at most 1.4, with [$a_1+a_2$] being the sum of the peak areas of peaks 1 and 2, and [$a_4+a_5+a_6$] being the sum of the peak areas of peaks 4, 5, and 6, and $a_3$ being the peak area of peak 3. These $^{29}$Si-NMR characteristics are understood as being determined according the Reference Example 4.4 of the present invention.
7. The molding of any of embodiments 1 to 6, having a water uptake in the range of from 3 to 8 weight-%, preferably from 4 to 7 weight-%. The water uptake is understood as being determined according to Reference Example 4.5 of the present invention.
8. The molding of any of embodiments 1 to 7, the infrared spectrum of said molding comprising a band in the region of (3700-3750)+/−20 cm$^{-1}$ and a band in the region of (3670-3690)+/−20 cm$^{-1}$, wherein the intensity ratio of the band in the region of (3700-3750)+/−20 cm$^{-1}$ relative to the band in the region of (3670-3690)+/−20 cm$^{-1}$ is at most 1.5, preferably at most 1.4. These IR characteristics are understood as being determined according the Reference Example 4.6 of the present invention.

Further, a preferred process for the preparation of said catalyst according to (ii) in the form of a micropowder and/or molding, comprising the ZnTiMWW, is characterized by the following features and embodiments, including the combinations of embodiments according to the given dependencies:
1. A process comprising
    (a) providing a suspension containing a microporous aluminum-free zeolitic material of structure type MWW containing titanium and zinc (ZnTiMWW);
    (b) subjecting the suspension provided in (a) to spray-drying to obtain a micropowder;
    (c) optionally calcining the micropowder obtained in (b), wherein the micropowder obtained in (b) or (c), preferably in (c), is preferably the micropowder according to any of said micropowder embodiments 1 to 14 as described above.
2. The process of embodiment 1, wherein the suspension provided in (a) has a solid content in the range of from 5 to 25 weight-%, preferably of from 10 to 20 weight-%, the suspension preferably being an aqueous suspension.
3. The process of embodiment 1 or 2, wherein the ZnTiMWW according to (a) contains zinc in an amount of from 1.0 to 2.0 weight-%, preferably of from 1.2 to 1.9 weight-%, calculated as Zn, and titanium in an amount of from 1.0 to 2.0 weight-%, preferably of from 1.2 to 1.8 weight-%, calculated as Ti and based on the weight of the ZnTiMWW.
4. The process of any of embodiments 1 to 3, wherein in (b), a spray-apparatus, preferably a spray-tower is used for spray-drying the suspension, said apparatus having at least one spray-nozzle, preferably at least one two-component nozzle, said nozzle having a diameter in the range of from 3.5 to 4.5 mm.
5. The process of any of embodiments 1 to 4, wherein in (b), a spray-apparatus, preferably a spray-tower is used for spray-drying the suspension, said apparatus being operated with a nozzle gas having a temperature in the range of from 20 to 50° C., preferably of from 20 to 30° C., and a drying gas having a temperature in the range of from 250 to 350° C., preferably of from 275 to 325° C., said nozzle gas preferably being an inert gas, more preferably technical nitrogen, and said drying gas preferably being an inert gas, more preferably technical nitrogen.

6. The process of any of embodiments 1 to 5, wherein in (c), the micropowder is calcined at a temperature in the range of from 600 to 700° C. for a duration in the range of from 0.5 to 6 h.
7. The process of any of embodiments 1 to 6, further comprising
   (d) shaping the micropowder obtained in (b) or (c) to obtain a molding;
   (e) optionally drying and/or calcining the molding obtained in (d).
8. The process of embodiment 7, wherein the shaping according to (d) comprises
   (aa) mixing the micropowder with a binder or a binder precursor, preferably a silica binder or a silica binder precursor, wherein the weight ratio of the ZnTiMWW contained in the micropowder relative to silica contained in or resulting from the silica binder is in the range of from 3:7 to 1:4, to obtain a mixture;
   (bb) shaping the mixture obtained in (aa) to obtain the molding, said shaping preferably comprising subjecting the mixture obtained in (aa) to extrusion from which preferably strands are obtained having a diameter preferably in the range of from 1.0 to 2.0 mm, more preferably of from 1.5 to 1.7 mm.
9. The process of embodiment 8, wherein in (aa), a carbohydrate and/or water is/are added as pasting agent.
10. The process of embodiment 8 or 9, wherein the mixing in (aa) is carried out for a duration in the range of from 15 to 60 min, preferably of from 30 to 55 min, more preferably of from 40 to 50 min.
11. The process of any of embodiments 7 to 10, wherein in (d), no mesopore-forming agent selected from the group consisting of polyalkylene oxides such as polyethylene oxides, polystyrene, polyacrylates, polymethacrylates, polyolefins, polyamides, and polyesters is added.
12. The process of any of embodiments 7 to 11, wherein in (e), the molding is dried at a temperature in the range of from 100 to 150° C. for a duration in the range of from 10 to 20 h and calcined at a temperature in the range of from 500 to 600° C. for a duration in the range of from 0.5 to 2 h.
13. The process of any of embodiments 7 to 12, further comprising
   (f) subjecting the molding obtained in (d) or (e), preferably in (e), to a water-treatment;
   (g) optionally drying and/or calcining the water-treated molding,
   wherein the molding obtained in (f) or (g), preferably in (g), is preferably the molding according to any of said molding embodiments 1 to 8 as described above.
14. The process of embodiment 13, wherein in (f), the water-treatment comprises treating the molding with liquid water in an autoclave under autogenous pressure at a temperature in the range of from 100 to 200° C., preferably of from 125 bis 175° C., more preferably of from 140 to 150° C. for a period of from 2 to 24 hours, preferably of from 6 to 10 h.
15. The process of embodiment 13 or 14, wherein in (f), the weight ratio of the molding relative to the water is in the range of from 0.02 to 0.08, preferably of from 0.03 to 0.07, more preferably of from 0.04 to 0.06.
16. The process of any of embodiments 13 to 15, wherein in (g), the water-treated molding is dried at a temperature in the range of from 100 to 150° C. for a duration in the range of from 10 to 20 h and calcined at a temperature in the range of from 400 to 500° C. for a duration in the range of from 1 to 3 h.
17. The process of any of embodiments 7 to 16, wherein the molding is not subjected to steaming.

Regarding said preferred process for the preparation of said catalyst according to (b) in the form of a micropowder and/or a molding, comprising the ZnTiMWW, described above by embodiments 1 to 17, the ZnTiMWW based on which the suspension in embodiment 1.(a) is provided, can be prepared according to all conceivable methods. For example, it is possible to prepare a microporous aluminum-free zeolitic material of structure type MWW containing titanium (TiMWW) and subject the TiMWW to a suitable treatment to obtain the ZnTiMWW. Further, it is possible to prepare an aluminum-free zeolitic material of structure type MWW (MWW) and subject the MWW to a suitable treatment to obtain the ZnTiMWW wherein, for example, both Zn and Ti are suitably incorporated in the MWW. Further, it is conceivable to prepare aluminum-free zeolitic material of structure type MWW wherein, during the synthesis of the MWW-type framework, Ti is introduced and the resulting material is subjected to a suitable treatment to incorporate Zn, or Zn is introduced and the resulting material is subjected to a suitable treatment to incorporate Ti, or both Zn and Ti are introduced. As conceivable methods for the preparation of TiMWW, the processes as described, for example, in U.S. Pat. No. 6,114,551, or in Wu et al., "Hydrothermal Synthesis of a novel Titanosilicate with MWW Topology", Chemistry Letters (2000), pp. 774-775 may be mentioned. Preferably, an aluminum-free zeolitic material of structure type MWW containing Ti (TiMWW) is prepared in a first stage, and in a second stage, the TiMWW is subjected to a suitable treatment to obtain the ZnTiMWW. More preferably, the ZnTiMWW is prepared according to a process comprising
(I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW.

Preferably, in stage (I), the B-MWW is prepared by a process whose preferred steps and conditions are defined by the following embodiments 1 to 28 and the respective dependencies as indicated:
1. A process for preparing an aluminum-free boron containing zeolitic material comprising the framework structure MWW (B-MWW), comprising
   (a) hydrothermally synthesizing a B-MWW precursor from a synthesis mixture containing water, a silicon source, a boron source, and an MWW template compound obtaining the B-MWW precursor in its mother liquor, the mother liquor having a pH above 9;
   (b) adjusting the pH of the mother liquor, obtained in (a) and containing the B-MWW precursor, to a value in the range of from 6 to 9;
   (c) separating the B-MWW precursor from the pH-adjusted mother liquor obtained in (b) by filtration in a filtration device.
2. The process of embodiment 1, wherein in (a), at least 95 weight-%, preferably at least 99 weight-%, more preferably at least 99.9 weight-% of the synthesis mixture consist of the water, the silicon source, the boron source, and the template compound.

3. The process of embodiment 1 or 2, wherein in (a), the silicon source is selected from the group consisting of fumed silica, colloidal silica, and a mixture thereof, the silicon source preferably being colloidal silica, more preferably ammonia-stabilized silica, the boron source is selected from the group consisting of boric acid, borates, boron oxide, and a mixture of two or more thereof, the boron source preferably being boric acid, and the MWW template compound selected from the group consisting of piperidine, hexamethylene imine, N,N,N,N',N',N'-hexamethyl-1,5-pentanediammonium ion, 1,4-bis(N-methylpyrrolidinium) butane, octyltrimethylammonium hydroxide, heptyltrimethylammonium hydroxide, hexyltrimethylammonium hydroxide, N,N,N-trimethyl-1-adamantyl-ammonium hydroxide, and a mixture of two or more thereof, the MWW template compound preferably being piperidine.

4. The process of any of embodiments 1 to 3, wherein in (a), the synthesis mixture contains the boron source, calculated as elemental boron, relative to the silicon source, calculated as elemental silicon, in a molar ratio in the range of from 0.4:1 to 2.0:1, preferably from 0.6:1 to 1.9:1, more preferably from 0.9:1 to 1.4:1, the water relative to the silicon source, calculated as elemental silicon, in a molar ratio in the range of from 1:1 to 30:1, preferably from 3:1 to 25:1, more preferably from 6:1 to 20:1; and the template compound relative to the silicon source, calculated as elemental silicon, in a molar ratio in the range of from 0.4:1 to 2.0:1, preferably from 0.6:1 to 1.9:1, more preferably from 0.9:1 to 1.4:1.

5. The process of any of embodiments 1 to 4, wherein in (a), the hydrothermal synthesizing is carried out at a temperature in the range of from 160 to less than 180° C., preferably from 170 to 175° C., for a period of time in the range of from 1 to 72 h, preferably from 6 to 60 h, more preferably from 12 to 50 h.

6. The process of any of embodiments 1 to 5, wherein in (a), the hydrothermal synthesizing is carried out at least partially under stirring.

7. The process of any of embodiments 1 to 6, wherein in (a), the synthesis mixture additionally contains a seeding material, preferably a zeolitic material comprising the framework structure MWW, more preferably a boron containing zeolitic material comprising the framework structure MWW.

8. The process of embodiment 7, wherein the synthesis mixture contains the seeding material, relative to the silicon source, in a weight ratio in the range of from 0.01:1 to 1:1, preferably from 0.02:1 to 0.5:1, more preferably from 0.03:1 to 0.1:1, calculated as amount of seeding material in kg relative to silicon contained in the silicon source calculated as silicon dioxide in kg.

9. The process of any of embodiments 1 to 8, wherein the pH of the mother liquor obtained from (a) is above 10, preferably in the range of from 10.5 to 12, more preferably from 11 to 11.5.

10. The process of any of embodiments 1 to 9, wherein in (b), the pH of the mother liquor obtained in (a) is adjusted to a value in the range of from 6.5 to 8.5, preferably from 7 to 8.

11. The process of any of embodiments 1 to 10, wherein in (b), the pH is adjusted by a method comprising
    (aa) adding an acid to the mother liquor obtained from (a) containing the B-MWW precursor, wherein the adding is preferably carried out at least partially under stirring.

12. The process of embodiment 11, wherein in (aa), the adding is carried out at a temperature in the range of from 20 to 70° C., preferably from 30 to 65° C., more preferably from 40 to 60° C.

13. The process of embodiment 11 or 12, wherein in (aa), the acid is an inorganic acid, preferably an aqueous solution containing the inorganic acid.

14. The process of embodiment 13, wherein the inorganic acid is selected from the group consisting of phosphoric acid, sulphuric acid, hydrochloric acid, nitric acid, and a mixture of two or more thereof, the inorganic acid preferably being nitric acid.

15. The process of any of embodiments 11 to 14, the method additionally comprising
    (bb) stirring the mother liquor to which the acid was added according to (aa), wherein during (bb), no acid is added to the mother liquor.

16. The process of embodiment 15, wherein in (bb), the stirring is carried out at a temperature in the range of from 20 to 70° C., preferably from 25 to 65° C., more preferably from 30 to 60° C.

17. The process of any of embodiments 1 to 16, wherein in (b), the size of the particles contained in the mother liquor, expressed by the respective Dv10, Dv50, and Dv90 value, is increased for at least 2%, preferably at least 3%, more preferably at least 4.5% regarding Dv10, for at least 2%, preferably at least 3%, more preferably at least 4.5% regarding Dv50, and for at least 5%, preferably at least 6%, more preferably at least 7% regarding Dv90.

18. The process of any of embodiments 1 to 17, wherein the pH-adjusted mother liquor obtained from (b) has a solids content in the range of from 1 to 10 weight-%, preferably from 4 to 9 weight-%, more preferably from 7 to 8 weight-%, based on the total weight of the pH-adjusted mother liquor obtained from (b).

19. The process of any of embodiments 1 to 18, wherein the pH-adjusted mother liquor obtained from (b) has a filtration resistance in the range of from 10 to 50 mPa*s/m$^2$, preferably from 15 to 45 mPa*s/m$^2$, more preferably from 20 to 40 mPa*s/m$^2$.

20. The process of any of embodiments 1 to 19, further comprising
    (d) washing the B-MWW precursor obtained from (c), preferably the filter cake obtained from (c), wherein the washing is preferably performed using water was washing agent.

21. The process of embodiment 20, wherein in (d), the filter cake obtained from (c) is has a washing resistance in the range of from 10 to 50 mPa*s/m$^2$, preferably from 15 to 45 mPa*s/m$^2$, more preferably from 20 to 40 mPa*s/m$^2$.

22. The process of embodiment 20 or 21, wherein the washing is carried out until the conductivity of the filtrate is at most 300 microSiemens/cm, preferably at most 250 microSiemens/cm, more preferably at most 200 microSiemens/cm.

23. The process of any of embodiments 1 to 22, further comprising
    (e) drying the B-MWW precursor obtained from (c), preferably from (d), at a temperature in the range of from 20 to 50° C., preferably from 20 to 40° C., more preferably from 20 to 30° C., wherein the drying is preferably carried out by subjecting the B-MWW to a gas stream, preferably a nitrogen stream.

24. The process of any of embodiments 1 to 23, wherein the residual moisture of the B-MWW precursor obtained from (c), preferably from (d), more preferably from (e), is in the range of from 80 to 90 weight-%, preferably from 80 to 85 weight-%.
25. The process of any of embodiments 1 to 24, further comprising
   (f) preparing a suspension, preferably an aqueous suspension, containing the B-MWW precursor obtained from to (c), preferably from (d), more preferably from (e), and having a solids content in the range of from 10 to 20 weight-%, preferably from 12 to 18 weight-%, more preferably from 14 to 16 weight-%;
   (g) spray drying the suspension obtained from (f) containing the B-MWW precursor, obtaining a spray powder;
   (h) calcining the spray powder obtained from (g) containing the B-MWW precursor, preferably at a temperature in the range of from 500 to 700° C., more preferably from 550 to 650° C., more preferably from 575 to 625° C. for a period of time in the range of from 1 to 24 h, preferably from 2 to 18 h, more preferably from 6 to 12 h, obtaining a spray powder of which at least 99 weight-%, more preferably at least 99.5 weight-% consist of the B-MWW.
26. The process of embodiment 25, wherein in (h), the calcining is carried out in continuous mode, preferably in a rotary calciner, preferably at a throughput in the range of from 0.5 to 20 kg spray powder per h.
27. The process of embodiment 25 or 26, wherein the degree of crystallinity of the B-MWW contained in the spray powder obtained from (h) is at least (75±5) %, preferably at least (80±5) %, as determined via XRD.
28. The process of any of embodiments 25 to 27, wherein the BET specific surface area of the B-MWW contained in the spray powder obtained from (h) is at least 300 m$^2$/g, preferably in the range of from 300 to 500 m$^2$/g, as determined according to DIN 66131.

Preferably, stage (II) is carried by a process whose preferred steps and conditions are defined by the following embodiments 1 to 7 and the respective dependencies as indicated:
1. A process for the preparation of a zeolitic material, comprising
   (a) providing the boron-containing zeolitic material of structure type MWW (B-MWW) obtained according to stage (I);
   (b) deboronating the B-MWW by treating the B-MWW with a liquid solvent system thereby obtaining a deboronated B-MWW (MWW);
   wherein the liquid solvent system is selected from the group consisting of water, monohydric alcohols, polyhydric alcohols, and mixtures of two or more thereof, and wherein said liquid solvent system does not contain an inorganic or organic acid or a salt thereof, the acid being selected from the group consisting of hydrochloric acid, sulfuric acid, nitric acid, phosphoric acid, formic acid, acetic acid, propionic acid, oxalic acid, and tartaric acid.
2. The process of embodiment 1, wherein the liquid solvent system does not contain an inorganic or organic acid, or a salt thereof.
3. The process of embodiment 1 or 2, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.
4. The process of any of embodiments 1 to 3, wherein the treating according to (b) is carried out at a temperature in the range of from 50 to 125° C.
5. The process of any of embodiments 1 to 4, wherein the treating according to (b) is carried out for a time in the range of from 6 to 20 h.
6. The process of any of embodiments 1 to 5, wherein the treating according to (b) is carried out in at least 2 separate steps, wherein between at least 2 treating steps, the MWW is dried, preferably at a temperature in the range of from 100 to 150° C.
7. The process of any of embodiments 1 to 6, further comprising
   (c) post-treating the MWW obtained from (b) by a process comprising
      (c.1) separating the MWW from the liquid solvent system;
      (c.2) preferably drying the separated MWW, preferably by spray-drying;
      (c.3) optionally calcining the MWW obtained from (c.1) or (c.2), preferably at temperatures in the range of from 500 to 700° C.

As far as stage (III) is concerned, preferably a suitable starting mixture, preferably an aqueous mixture, containing the MWW and a Ti containing precursor, and preferably containing at least one suitable micropore-forming agent, is subjected to hydrothermal crystallization under autogenous pressure. It may be conceivable to use at least one suitable seeding material. As suitable Ti containing precursor, tetraalkylorthotitanates such as tetrabutyl orthotitanate may be mentioned by way of example. As suitable microporeforming agent, piperidine, hexamethylene imine, or mixtures of piperidine and hexamethylene imine may be mentioned by way of example. Preferably, the crystallization time is in the range of from 4 to 8 days, more preferably from 4 to 6 days. During hydrothermal synthesis, the crystallization mixture may be stirred. The temperatures applied during crystallization are preferably in the range of from 160 to 200° C., more preferably from 160 to 180° C. After hydrothermal synthesis, the obtained crystalline zeolitic material TiMWW is preferably suitably separated from the mother liquor. All methods of separating the TiMWW from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the TiMWW is preferably separated from its mother liquid by filtration to obtain a filter cake which is preferably subjected to washing, preferably with water. Subsequently, the filter cake, optionally further processed to obtained a suitable suspension, is subjected to spray drying or to ultrafiltration. Prior to separating the TiMWW from its mother liquor, it is possible to increase the TiMWW content of the mother liquor by concentrating the suspension. If washing is applied, it is preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. After separation of the TiMWW from its mother liquor, preferably achieved via filtration, and after washing, the washed filter cake containing the TiMWW is preferably subjected to pre-drying, for example by subjecting the filter cake to a suitable gas stream, preferably a nitrogen stream, for a time preferably in the range of from 4 to 10 h, more preferably from 5 to 8 h. Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. After drying, the TiMWW may be subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air. Preferably, no calcination is carried out according to (III).

Preferably, stages (III) and (IV) are carried out by a process whose preferred steps and conditions are defined by the following embodiments 1 to 27 and the respective dependencies as indicated:

1. A process for the preparation of a titanium-containing zeolitic material having an MWW framework structure comprising
   (a) providing the deboronated crystalline zeolitic material MWW obtained according to stage (II);
   (b) incorporating titanium into the zeolitic material provided in (a) comprising
     (b.1) preparing an aqueous synthesis mixture containing the zeolitic material provided in (i), an MWW template compound and a titanium source, wherein the molar ratio of the MWW template compound relative to Si, calculated as $SiO_2$ and contained in the zeolitic material provided in (a), is in the range of from 0.5:1 to 1.4:1;
     (b.2) hydrothermally synthesizing a titanium-containing zeolitic material having an MWW framework structure from the aqueous synthesis mixture prepared in (b.1), obtaining a mother liquor comprising the titanium-containing zeolitic material having an MWW framework structure;
   (c) spray-drying the mother liquor obtained from (b.2) comprising the titanium-containing zeolitic material having an MWW framework structure.
2. The process of embodiment 1, wherein in (b.1), the MWW template compound is selected from the group consisting of piperidine, hexamethylene imine, N,N,N,N', N',N'-hexamethyl-1,5-pentanediammonium ion, 1,4-bis (N-methylpyrrolidini-um)butane, octyltrimethylammonium hydroxide, heptyltrimethylammonium hydroxide, hexyltrimethylammonium hydroxide, and a mixture of two or more thereof, the MWW template compound preferably being piperidine.
3. The process of embodiment 1 or 2, wherein in (b.1), the titanium source is selected from the group consisting of tetrabutyl orthotitanate, tetraisopropyl orthotitanate, tetraethyl orthotitanate, titanium dioxide, titanium tetrachloride, titanium tert-butoxide, and a mixture of two or more thereof, the titanium source preferably being tetrabutyl orthotitanate.
4. The process of any of embodiments 1 to 3, wherein in the aqueous synthesis mixture in (b.1), the molar ratio of Ti, calculated as $TiO_2$ and contained in the titanium source, relative to Si, calculated as $SiO_2$ and contained in the zeolitic material having a molar ratio $B_2O_3:SiO_2$ of at most 0.02:1, is in the range of from 0.005:1 to 0.1:1, preferably from 0.01:1 to 0.08:1, more preferably from 0.02:1 to 0.06:1.
5. The process of any of embodiments 1 to 4, wherein in the aqueous synthesis mixture in (b.1), the molar ratio of $H_2O$ relative to Si, calculated as $SiO_2$ and contained in the zeolitic material having a molar ratio $B_2O_3:SiO_2$ of at most 0.02:1, is in the range of from 8:1 to 20:1, preferably from 10:1 to 18:1, more preferably from 12:1 to 16:1.
6. The process of any of embodiments 1 to 5, wherein in the aqueous synthesis mixture in (b.1), the molar ratio of the MWW template compound relative to Si, calculated as $SiO_2$ and contained in the zeolitic material provided in (i), is in the range of from 0.5:1 to 1.7:1, preferably from 0.8:1 to 1.5:1, more preferably from 1.0:1 to 1.3:1.
7. The process of any of embodiments 1 to 6, wherein in (b.2), the hydrothermal synthesizing is carried out at a temperature in the range of from 80 to 250° C., preferably from 120 to 200° C., more preferably from 160 to 180° C.
8. The process of any of embodiments 1 to 7, wherein in (b.2), the hydrothermal synthesizing is carried out for a period in the range of from 10 to 100 h, more preferably from 20 to 80 h, more preferably from 40 to 60 h.
9. The process of any of embodiments 1 to 8, wherein in (b.2), the hydrothermal synthesizing is carried out in a closed system under autogenous pressure.
10. The process of any of embodiments 1 to 9, wherein neither during (b.2), nor after (b.2) and before (c), the titanium-containing zeolitic material having an MWW framework structure is separated from its mother liquor.
11. The process of any of embodiments 1 to 10, wherein the mother liquor subjected to (c) comprising the titanium-containing zeolitic material having an MWW framework structure has a solids content, optionally after concentration or dilution, in the range of from 5 to 25 weight-%, more preferably from 10 to 20 weight-%, based on the total weight of the mother liquor comprising the titanium-containing zeolitic material.
12. The process of any of embodiments 1 to 11, wherein during spray-drying in (c), the drying gas inlet temperature is in the range of from 200 to 350° C. and the drying gas outlet temperature is in the range of from 70 to 190° C.
13. The process of any of embodiments 1 to 12, wherein the zeolitic material having an MWW framework structure obtained from (c) has a Si content in the range of from 30 to 40 weight-%, calculated as elemental Si, a total organic carbon content (TOC) in the range of from 0 to 14 weight-%, and a Ti content of from 2.1 to 2.8 weight-%, calculated as elemental titanium, in each case based on the total weight of the zeolitic material.
14. The process of any of embodiments 1 to 13, further comprising
   (d) treating the titanium-containing zeolitic material having an MWW framework structure obtained from (iii) with an aqueous solution having a pH of at most 5.
15. The process of embodiment 14, wherein after (c) and before (d), the spray-dried titanium-containing zeolitic material having an MWW framework structure obtained from (c) is not subjected to calcination.
16. The process of embodiment 14 or 15, wherein in (d), the weight ratio of the aqueous solution relative to the titanium-containing zeolitic material having an MWW framework structure is in the range of from 10:1 to 30:1, preferably from 15:1 to 25:1, more preferably from 18:1 to 22:1.
17. The process of any of embodiments 14 to 16, wherein in (d), the aqueous solution comprises an inorganic acid, preferably selected from the group consisting of phosphoric acid, sulphuric acid, hydrochloric acid, nitric acid, and a mixture of two or more thereof, the aqueous solution preferably comprising nitric acid.

18. The process of any of embodiments 14 to 17, wherein in (d), the aqueous solution has a pH in the range of from 0 to 5, preferably from 0 to 3, more preferably from 0 to 2.
19. The process of any of embodiments 14 to 18, wherein in (d), the titanium-containing zeolitic material having an MWW framework structure is treated with the aqueous solution at a temperature in the range of from 50 to 175° C., preferably from 70 to 125° C., more preferably from 95 to 105° C.
20. The process of any of embodiments 14 to 19, wherein in (d), the titanium-containing zeolitic material having an MWW framework structure is treated with the aqueous solution for a period in the range of from 0.1 to 6 h, preferably from 0.3 to 2 h, more preferably from 0.5 to 1.5 h.
21. The process of any of embodiments 14 to 20, wherein the treating according to (d) is carried out in a closed system under autogenous pressure.
22. The process of any of embodiments 14 to 21, further comprising
    (e) separating the titanium-containing zeolitic material having an MWW framework structure obtained from (d) from the aqueous solution, optionally followed by washing the separated titanium-containing zeolitic material having an MWW framework.
23. The process of embodiment 22, wherein (e) comprises drying the separated and optionally washed titanium-containing zeolitic material having an MWW framework structure.
24. The process of any of embodiments 14 to 23, further comprising
    (f) preparing a suspension, preferably an aqueous suspension containing the titanium-containing zeolitic material having an MWW framework structure obtained from (d), preferably from (e), said suspension having a solids content preferably in the range of from 5 to 25 weight-%, more preferably from 10 to 20 weight-%, based on the total weight of the suspension, and subjecting the suspension to spray-drying.
25. The process of embodiment 24, wherein during spray-drying, the drying gas inlet temperature is in the range of from 200 to 330° C. and the drying gas outlet temperature is in the range of from 120 to 180° C.
26. The process of any of embodiments 14 to 25, further comprising
    (g) calcining the titanium containing zeolitic material having an MWW framework structure obtained from (d), preferably from (e), more preferably from (f), wherein the calcining is preferably carried out at a temperature in the range of from 400 to 800° C., more preferably from 600 to 700° C.
27. The process of embodiment 26, wherein in (vii), the calcining is carried out in continuous mode, preferably with a rate in the range of from 0.2 to 2.0 kg zeolitic material per hour, more preferably from 0.5 to 1.5 kg zeolitic material per hour.

According to stage (V), the TiMWW preferably obtained according to stage (IV) is subjected to a suitable Zn treatment to obtain the ZnTiMWW used for the preparation of the suspension according to (a). Generally, as far as (V) is concerned, no specific restrictions exist provided that above-defined preferred ZnTiMWW can be obtained having the preferred Zn and Ti content. Most preferably, stage (V) comprises at least one suitable impregnation stage, more preferably at least one wet impregnation stage. Concerning this impregnation stage, it is preferred to contact the TiMWW preferably as obtained according to (IV) is contacted with at least one suitable Zn-containing precursor in at least one suitable solvent (wet impregnation), most preferably water. As suitable Zn-containing precursor, water-soluble Zn salts are especially preferred, with zinc acetate dihydrate being especially preferred. It is further preferred to prepare a solution of the Zn-containing precursor, preferably an aqueous solution, and to suspend the TiMWW in this solution. Further preferably, impregnation is carried out at elevated temperatures, relative to room temperature, preferably in the range of from 75 to 125° C., more preferably from 85 to 115° C., for a time preferably in the range of from 3.5 to 5 h, more preferably from 3 to 6 h. Stirring the suspension during impregnation is preferred. After the impregnation, the obtained ZnTiMWW is preferably suitably separated from the suspension. All methods of separating the ZnTiMWW from the suspension are conceivable. Especially preferably, separation is carried out via filtration, ultrafiltration, diafiltration or centrifugation methods. A combination of two or more of these methods can be applied. According to the present invention, the ZnTiMWW is preferably separated from the suspension by filtration to obtain a filter cake which is preferably subjected to washing, preferably with water. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. Subsequently, the preferably washed filter cake is subjected to pre-drying, for example by subjecting the filter cake to a suitable gas stream, preferably a nitrogen stream, for a time preferably in the range of from 5 to 15 h, more preferably from 8 to 12.

An especially preferred process for the preparation of a preferred catalyst according to step (ii) of the process of the present invention in the form of a molding, comprising the ZnTiMWW, and the respective characterization of this catalyst is described in Reference Example 2 of the present invention. A preferred process for the preparation of a preferred catalyst according to step (ii) of the process of the present invention in the form of a molding, comprising the TiMWW, and the respective characterization of this catalyst is described in Reference Example 3 of the present invention.

Epoxidation Reaction

According to step (ii) of the process of the present invention, the liquid feed stream provided in (i) is passed into an epoxidation reactor comprising a catalyst comprising the titanium zeolite of framework structure type MWW, and the liquid feed stream is subjected to epoxidation reaction conditions in the epoxidation reactor. During the epoxidation reaction, a reaction mixture is formed which comprises propylene oxide, acetonitrile, water, potassium dihydrogen phosphate, optionally propene, and optionally propane.

Generally, the continuous epoxidation reaction in (ii) can be carried out in any appropriate way. Preferably, the reaction in (ii) is carried out in at least one continuously operated reactor such as a tube reactor or a tube bundle reactor which preferably contains at least one cooling jacket surrounding the at least one tube. If the reaction in (ii) is carried out in such a reactor containing at least one cooling jacket, the term "reaction temperature" as used herein refers to the temperature of the cooling medium when entering the cooling jacket.

The catalyst comprising the titanium zeolite of framework structure type MWW can be employed in every conceivable form described hereinabove, including a powder, a micro-powder, preferably a spray-powder, as a molding comprising a powder, or as a molding comprising micropowder, preferably a spray-powder. Preferably, the catalyst comprising the titanium zeolite of framework structure type MWW is employed as a molding comprising a powder or a micropowder, preferably a spray-powder, more preferably as a molding comprising a micropowder, preferably a spray-powder. Regarding a preferred micropowder, reference is made to the micropowder characterized by the respective micropowder embodiments 1 to 14 hereinabove. Regarding a preferred molding, reference is made to the molding characterized by the respective molding embodiments 1 to 8 hereinabove.

The catalyst used in step (ii) of the present invention can be arranged in the reactor in every conceivable manner. Preferably, the catalyst is arranged as fluidized bed or as fixed bed, more preferably as fixed bed. Therefore, the present invention also relates to the process as described above, wherein in (ii), the catalyst comprising a titanium zeolite of framework structure type MWW is present in the reactor as fixed-bed catalyst.

As mentioned above, the liquid feed stream provided in (i) is passed into the reactor in (i) and passed the catalyst preferably present as fixed bed. During the epoxidation reaction, the catalyst loading is preferably in the range of from 0.05 to 1.25 $h^{-1}$, preferably from 0.1 to 1 $h^{-1}$, more preferably from 0.2 to 0.7 $h^{-1}$, wherein the catalyst loading is defined as the ratio of the mass flow rate in kg/h of hydrogen peroxide contained in liquid feed stream provided in (i) divided by the amount in kg of catalyst comprising a titanium zeolite of structure type MWW comprised in the epoxidation reactor in (ii). The term "the epoxidation conditions comprise" as used in this context of the present invention relates to an epoxidation reaction in step (ii) wherein in at least 90%, preferably at least 95% of the catalyst bed in the reactor and during at least 90%, preferably at least 95% of the overall reaction time, the catalyst loading is in the above-defined ranges.

During the epoxidation reaction in (ii), the temperature of the reaction mixture in the reactor is preferably controlled, more preferably kept in preferred ranges. In order to control the temperature of the reaction mixture, internal and/or external temperature control means can be used. The term "intern temperature control means" as used in this context of the present invention relate to means which are arranged in the reactor. The term "external temperature control means" as used in this context of the present invention relate to means which are arranged outside the reactor. Preferably, the temperature of the reaction mixture is controlled by external temperature control means, more preferably via a heat transfer medium which is preferably passed through a suitable jacket, which jacket preferably surrounds the reactor. In case a tube-bundle reactor is used as reactor, the jacket preferably surrounds all tubes of the tube-bundle. Therefore, the present invention relates to the process as described above, wherein during subjecting the liquid feed stream provided in (i) to epoxidation reaction conditions in (ii), the temperature of the reaction mixture is controlled using a heat transfer medium, preferably by passing the heat transfer medium through a jacket of the epoxidation reactor.

Preferably, during the epoxidation reaction in (ii), the reaction temperature is in the range of from 20 to 100° C., more preferably from 25 to 90° C., more preferably from 30 to 80° C., more preferably from 35 to 70° C., more preferably from 40 to 60° C. The term "reaction temperature" as used in this context of the present invention relates to the temperature of the heat transfer medium prior to controlling of the temperature of the reaction mixture, preferably to the temperature of the heat transfer medium at the entrance of the jacket of the epoxidation reactor, through which jacket the heat transfer medium is passed. Therefore, the present invention relates to the process as described above, wherein in (ii), the epoxidation conditions comprise, preferably consist of an epoxidation reaction temperature in the range of from 20 to 100° C., preferably from 30 to 80° C., more preferably from 40 to 60° C., wherein the epoxidation reaction temperature is defined as the temperature of the heat transfer medium prior to controlling of the temperature of the reaction mixture, preferably as the temperature of the heat transfer medium at the entrance of the jacket of the epoxidation reactor. The term "the epoxidation conditions comprise" as used in this context of the present invention relate to an epoxidation reaction in step (ii) wherein for at least 98%, preferably at least 99%, more preferably at least 99.9% of the overall reaction time, the reaction temperature is in the above-defined ranges. The term "overall reaction time" as used in this context of the present invention relates to the reaction time a given catalyst bed is used before it is either discarded or subjected to regeneration. In particular at the beginning of an epoxidation reaction in (ii) when the catalyst is fresh, i.e. at the start-up of the epoxidation reaction in (ii), the reaction temperature can be outside the above-mentioned ranges for a short period of time. Preferably, the flow rate of the heat transfer medium is chosen so that the temperature difference between its inlet temperature and its outlet temperature is at most 3 K, more preferably at most 2 K, more preferably at most 1 K.

Preferably, during the epoxidation reaction in (ii), the epoxidation reaction pressure is in the range of from 14 to 100 bar, more preferably from 14.5 to 50 bar, more preferably from 15 to 32 bar, more preferably from 15 to 25 bar. The term "epoxidation reaction pressure" as used in this context of the present invention relates to the pressure at the exit of the epoxidation reactor where the effluent is removed from the reactor according to (iii). Therefore, the present invention relates to the process as described above, wherein in (ii), the epoxidation conditions comprise, preferably consist of an epoxidation reaction pressure in the range of from 14 to 100 bar, preferably from 15 to 32 bar, more preferably from 15 to 25 bar. The term "the epoxidation conditions comprise" as used in this context of the present invention relate to an epoxidation reaction in step (ii) wherein for at least 98%, preferably at least 99%, more preferably at least 99.9% of the overall reaction time, the reaction temperature is in the above-defined ranges. The term "overall reaction time" as used in this context of the present invention relates to the reaction time a given catalyst bed is used before it is either discarded or subjected to regeneration.

Preferably, the epoxidation reaction according to step (ii) of the present invention is carried out at an essentially constant hydrogen peroxide conversion. Preferably, in order to determine the hydrogen peroxide conversion, the molar flow rate of hydrogen peroxide in the effluent stream removed in (iii), referred to herein as $m_{out}$, is compared with the molar flow rate of hydrogen peroxide in the liquid feed stream provided in (i), referred to herein as $m_{in}$, and wherein the hydrogen peroxide conversion is defined as $100 \times (1 - m_{out}/m_{in})$. Preferably, the inlet temperature of the heat transfer medium described above is adjusted in the above-mentioned preferred ranges in order to keep the hydrogen peroxide conversion essentially constant in the range of from 80 to 100%, more preferably from 90 to 100%, more preferably from 95 to 100%, more preferably from 99 to 100%, more preferably from 99.5 to 100%, more preferably from 99.9 to 100%.

Therefore, the present invention relates to the process as described above, wherein in (ii), the epoxidation conditions comprise a hydrogen peroxide conversion in the range of from 80 to 100%, preferably from 90 to 100%, more preferably from 99 to 100%, more preferably from 99.5 to 100%, more preferably from 99.9 to 100%, wherein the hydrogen peroxide conversion is calculated based on the amount of hydrogen peroxide comprised in the effluent stream removed in (iii) and the amount of hydrogen peroxide comprised in the liquid feed stream provided in (i). The term "the epoxidation conditions comprise" as used in this context of the present invention relate to an epoxidation reaction in step (ii) wherein for at least 98%, preferably at least 99%, more preferably at least 99.9% of the overall reaction time, the hydrogen peroxide conversion is in the above-defined ranges. The term "overall reaction time" as used in this context of the present invention relates to the reaction time a given catalyst bed is used before it is either discarded or subjected to regeneration. In particular at the beginning of an epoxidation reaction in (ii) when the catalyst is fresh, i.e. at the start-up of the epoxidation reaction in (ii), the hydrogen peroxide conversion can be outside the above-mentioned ranges for a short period of time. Preferably, the reaction temperature is not kept constant during the reaction but is adjusted continuously or step-wise to allow for a constant hydrogen peroxide conversion. Generally, due to a certain catalyst deactivation, the reaction temperature is continuously or step-wise increased. Preferably, the reaction temperature is continuously or step-wise increased by 1 K/d (Kelvin/day) at most, more preferably by less than 1 K/d.

Preferably, the reaction mixture which is present in the reactor in (ii) is liquid under the epoxidation conditions. Preferably, the reaction mixture consists of one single liquid phase, of two liquid phases, or of three or more liquid phases. Preferably, the reaction mixture in the reactor in (ii) consists of one single liquid phase or of two liquid phases, more preferably of one single liquid phase.

Generally, the reactor used in step (ii) of the present invention can be arranged horizontally or vertically. Preferably, the reactor is arranged vertically. In the preferably vertically arranged reactor, the liquid feed stream provided in (i) can be passed in up-flow mode or on down-flow mode, the up-flow mode being preferred. Preferably, compared with the direction of the flow of the liquid feed stream, the heat transfer medium is passed through the jacket in co-current mode.

Generally, the epoxidation reaction in (ii) can be carried out in one or more reactors wherein these reactors can be arranged in parallel or in series. Preferably, the reaction in (ii) is carried out in one reactor or in at least two reactors, preferably two reactors, which are arranged in series wherein between two reactors arranged in series, a suitable intermediate treatment can be carried out. If the reaction is carried out in two reactors arranged in series, it is preferred that the first reactor is operated as described above, i.e. as isothermal reactor, and the second reactor, i.e. the downstream reactor, is operated as adiabatic or essentially adiabatic reactor. The term "reactor" as used herein also encompasses two or more reactors arranged in parallel wherein a feed stream passed is divided in two or more sub-streams, each substream is passed into a reactor, and the effluent streams removed from the reactors are combined to obtain the overall effluent stream. Therefore, the epoxidation reaction can be carried out in at least one first reactor such as two or more first reactors, for example 2, 3, 4 first reactors, which are arranged in parallel and which are preferably isothermal reactors, and in at least one second reactor such as two or more second reactors, for example 2, 3, 4 second reactors, which are arranged in parallel and which are preferably adiabatic or essentially adiabatic reactors.

If the epoxidation reaction according to (ii) is carried out in two reactors arranged in series, it is preferred that in the first reactor which is preferably an isothermal reactor, the hydrogen peroxide conversion is kept essentially constant in a range of from 80 to 99%, preferably from 85 to 98%, more preferably from 90 to 97%, and in the second reactor which is preferably designed as adiabatic or essentially adiabatic reactor, the overall hydrogen peroxide conversion, i.e. the hydrogen peroxide conversion taking into account the conversion in the first and the second reactor, is brought to a value of more than 99%, preferably at least 99.5%, more preferably at least 99.9%.

In case the reaction according to (ii) is carried out in two reactors arranged in series without intermediate treatment, it is preferred that the reaction comprises
(i) providing a liquid feed stream comprising propene, hydrogen peroxide, acetonitrile, water, dissolved potassium dihydrogen phosphate, and optionally propane;
(ii-1) passing the liquid feed stream provided in (i) into an epoxidation reactor comprising a catalyst comprising a titanium zeolite of framework structure type MWW, and subjecting the liquid feed stream to epoxidation reaction conditions in the epoxidation reactor, obtaining a stream leaving the epoxidation reactor, said stream comprising propylene oxide, acetonitrile, water, potassium dihydrogen phosphate, optionally propane, optionally propene, and unreacted hydrogen peroxide, wherein the epoxidation reactor is preferably operated as isothermal reactor;
(ii-2) passing the stream leaving the epoxidation reaction according to (ii-1), preferably after admixing with propene optionally admixed with propane, into an epoxidation reactor comprising a catalyst comprising a titanium zeolite of framework structure type MWW, and subjecting the liquid feed stream to epoxidation reaction conditions in the epoxidation reactor, obtaining a stream leaving the epoxidation reactor, said stream comprising propylene oxide, acetonitrile, water, potassium dihydrogen phosphate, optionally propene, and optionally propane; wherein the epoxidation reactor is preferably operated as adiabatic or essentially adiabatic reactor;
(iii) removing the stream obtained in (ii-2) as effluent stream, the effluent stream comprising propylene oxide, acetonitrile, water, potassium dihydrogen phosphate, optionally propene, and optionally propane;
wherein the concentration of the dissolved potassium dihydrogen phosphate in the liquid feed stream provided in (i) is at least 10%, preferably the range of from 10 to 100%, preferably from 20 to 100%, more preferably from 30 to 100%, more preferably from 40 to 100%, more preferably from 50 to 100%, more preferably from 60 to 100%, more preferably from 70 to 100%, more preferably from 80 to 100% of the solubility limit of the potassium dihydrogen phosphate in the liquid feed stream.

For this case where the reaction according to (ii) is carried out in two reactors arranged in series without intermediate treatment, the two reactors arranged in series can be designed as one reactor comprising two reaction zones, wherein the first reaction zone according to (ii-1) is preferably designed as an isothermal reaction zone and the second, downstream reaction zone according to (ii-2) is preferably designed as an adiabatic or essentially adiabatic reaction zone.

In case the reaction according to (ii) is carried out in two reactors arranged in series with intermediate treatment, it is preferred that the reaction comprises (i) providing a liquid feed stream comprising propene, hydrogen peroxide, acetonitrile, water, dissolved potassium dihydrogen phosphate, and optionally propane;

(ii-1) passing the liquid feed stream provided in (i) into an epoxidation reactor comprising a catalyst comprising a titanium zeolite of framework structure type MWW, and subjecting the liquid feed stream to epoxidation reaction conditions in the epoxidation reactor, obtaining a stream leaving the epoxidation reactor, said stream comprising propylene oxide, acetonitrile, water, potassium dihydrogen phosphate, optionally propane, optionally propene, and unreacted hydrogen peroxide, wherein the epoxidation reactor is preferably operated as isothermal reactor;

(ii-2) separating propylene oxide from the stream obtained from (ii-1), obtaining a stream being enriched in propylene oxide and depleted of hydrogen peroxide, and a stream being depleted of propylene oxide and comprising unreacted hydrogen peroxide, acetonitrile, and water;

(ii-3) passing the stream being depleted of propylene oxide and comprising unreacted hydrogen peroxide, acetonitrile, and water, preferably after admixing with propene optionally admixed with propane, into an epoxidation reactor comprising a catalyst comprising a titanium zeolite of framework structure type MWW, and subjecting the liquid feed stream to epoxidation reaction conditions in the epoxidation reactor, obtaining a stream leaving the epoxidation reactor, said stream comprising propylene oxide, acetonitrile, water, potassium dihydrogen phosphate, optionally propene, and optionally propane; wherein the epoxidation reactor is preferably operated as adiabatic or essentially adiabatic reactor;

(ii-4) preferably combining the stream being enriched in propylene oxide and depleted of hydrogen peroxide obtained in (ii-2) and the stream obtained in (ii-3);

(iii) removing the stream obtained in (ii-3), preferably the combined stream obtained in (ii-4), as effluent stream, the effluent stream comprising propylene oxide, acetonitrile, water, potassium dihydrogen phosphate, optionally propene, and optionally propane;

wherein the concentration of the dissolved potassium dihydrogen phosphate in the liquid feed stream provided in (i) is at least 10%, preferably the range of from 10 to 100%, preferably from 20 to 100%, more preferably from 30 to 100%, more preferably from 40 to 100%, more preferably from 50 to 100%, more preferably from 60 to 100%, more preferably from 70 to 100%, more preferably from 80 to 100% of the solubility limit of the potassium dihydrogen phosphate in the liquid feed stream.

According to this process where in the intermediate treatment in (ii-2), propylene oxide is separated from the stream obtained from (ii-1), the separation is preferably carried out via distillation. Preferably, the stream leaving the epoxidation reactor according to (ii-1), said stream comprising propylene oxide, acetonitrile, water, potassium dihydrogen phosphate, optionally propane, optionally propene, and unreacted hydrogen peroxide, is subjected to a suitable pressure release stage and passed to the preferred distillation according to (ii-2). Optionally, the possibly formed gaseous and liquid phases are suitably separated and passed to different trays of the distillation tower employed according to (ii-2). Alternatively, the effluent stream can be subjected to said pressure release directly in the distillation column employed according to (ii-2). Preferably, the distillation according to (ii-2) is carried out so that at most 10% of the propylene oxide comprised in the stream obtained from (ii-1) are comprised in the top stream, and at least 95%, preferably at least 98% of the hydrogen peroxide comprised in the stream obtained from (ii-1) are comprised in the bottoms stream. The bottoms stream is then preferably passed according to (ii-3) to the downstream epoxidation reactor where, preferably after admixing propene, the overall hydrogen peroxide conversion is brought to a value of more than 99%, preferably at least 99.5%, more preferably at least 99.9%. In order to achieve the desired hydrogen peroxide conversion, it is possible to suitably adjust the temperature of the stream to be fed to the downstream epoxidation reactor which is preferably an adiabatic or essentially adiabatic reactor.

Step (iii)

Preferably, the effluent stream removed in (iii) comprises the propylene oxide in amount of from 5 to 20 weight-%, preferably from 8 to 18 weight-%, more preferably 10 to 14 weight-% based on the total weight of the effluent stream; the acetonitrile in amount of from 60 to 75 weight-%, preferably from 60 to 65 weight-%, based on the total weight of the effluent stream;

the water in amount of from 10 to 25 weight-%, preferably from 15 to 20 weight-%, based on the total weight of the effluent stream;

optionally the propene with a molar ratio of propene relative to hydrogen peroxide comprised in the feed stream in the range of from 0.005:1 to 0.7:1, preferably from 0.25:1 to 0.45:1;

the dissolved potassium dihydrogenphosphate with a molar ratio of potassium dihydrogenphosphate relative to hydrogen peroxide comprised in the feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1; and optionally the propane, preferably in an amount in the range of from 95 to 100%, preferably from 98 to 100%, more preferably from 99 to 100% of the amount contained in the liquid feed stream provided in (i);

wherein at least 95 weight-%, preferably from 95 to 100 weight-%, more preferably from 98 to 100 weight-% of the effluent stream removed in (iii) consist of propylene oxide, acetonitrile, water, potassium dihydrogenphosphate, optionally propene, and optionally propane.

Preferably, at least 95 weight-%, more preferably from 95 to 100 weight-%, more preferably from 98 to 100 weight-% of the effluent stream removed in (iii) consist of propylene oxide, acetonitrile, water, potassium dihydrogenphosphate, optionally propene, and optionally propane.

Preferably, the effluent stream removed in (iii) comprises potassium with a molar ratio of potassium relative to hydrogen peroxide comprised in the feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1.

In addition to the major components described above, the effluent stream removed in (iii) may contain at least one further by-product or side-product of the epoxidation reaction or at least compound which is formed in additional work-up stages and which is recycled into the epoxidation reaction in the course of the continuous reaction. Such a by-product or side-product may include, for example, oxygen, or at least one propylene glycol. Therefore, the present invention relates to the process as described above, wherein the effluent stream removed in (iii) comprises contains molecular oxygen, preferably with a molar ratio of the molecular oxygen comprised in the effluent stream removed in (iii) relative to the hydrogen peroxide comprised in the liquid feed stream provided in (i) in the range of from 0.05:100 to 2.5:100, preferably from 0.1:100 to 2.25:100, more preferably from 0.15:100 to 42:100.

According to the present invention, the effluent stream removed according to (iii) may contain at least one component B wherein the normal boiling point of the at least one component B is higher than the normal boiling point of acetonitrile and wherein the decadic logarithm of the octanol-water partition coefficient (log $K_{OW}$) of the at least one component B is greater than zero. Regarding the determination of the octanol-water partition coefficient, reference is made to Reference Example 5 hereinbelow. Typically, the at least one component B contained in the effluent stream removed according to (iii) either is a by-product and/or a side-product obtained during the epoxidation reaction in (ii), and/or is a compound which is formed during at least one of the work-up stages being preferably carried out downstream of step (ii) and which accumulates if certain process streams of the preferred integrated process are recycled into (i), and/or is contained as an impurity in at least one of the starting materials employed in (i) such as an impurity in the acetonitrile or an impurity in the hydrogen peroxide. Preferably, the at least one component B is propionitrile, 1-nitropropane, 2-nitropropane, 3-methylbutanenitrile, n-pentanenitrile, 1-pentanol, 2-pentanol, 2-butanone, 2-pentanone, 2-hexanone, 4-methyl-2-heptanone, 2,6-dimethyl-4-heptanol, 4,6-dimethyl-2-heptanol, 2,6-dimethyl-4-heptanone, 4,6-dimethyl-2-heptanone, 2,6-dimethyl-4,6-heptandiol, 2,4-dimethyloxazoline, 2,5-dimethyloxazoline, cis-2,4-dimethyl-1,3-dioxolane, trans-2,4-dimethyl-1,3-dioxolane, at least one impurity contained in the hydrogen peroxide stream employed in (i), or a combination of two or more of these compounds. Preferably, the at least one impurity contained in the hydrogen peroxide stream employed in (i) is an alkyl phosphate such as tris-(2-ethylhexyl) phosphate, a nonyl alcohol such as diisobutylcarbinol, an alkylcyclohexanol ester such as 2-methyl-cyclohexylacetate, an N,N-dialkyl carbonamide such as N,N-dibutylpropionamide, an N-alkyl-N-aryl carbonamide such as N-ethyl-N-phenylbenzamide, an N,N-dialkyl carbamate such as 2-ethylhexyl-N-butylcarbamate, a tetraalkyl urea such as tetra-n-butylurea, a cyclic urea derivative such as 1,3-dihexyltetrahydro-2(1H)-pyrimidone, a phenylalkyl urea such as N,N-dibutyl-N'-methyl-N'-phenylurea, an N-alkyl-2-pyrrolidone such as octyl pyrrolidone, an N-alkyl caprolactam such as n-octyl caprolactam, or a combination of two or more of these compounds.

Therefore, the present invention relates to the process as described above, wherein the effluent stream removed in (iii) comprises
the propylene oxide in amount of from 5 to 20 weight-%, preferably from 8 to 18 weight-%, more preferably 10 to 14 weight-% based on the total weight of the effluent stream;
the acetonitrile in amount of from 60 to 75 weight-%, preferably from 60 to 65 weight-%, based on the total weight of the effluent stream;
the water in amount of from 10 to 25 weight-%, preferably from 15 to 20 weight-%, based on the total weight of the effluent stream;
optionally the propene with a molar ratio of propene relative to hydrogen peroxide comprised in the feed stream in the range of from 0.005:1 to 0.7:1, preferably from 0.25:1 to 0.45:1;
the dissolved potassium dihydrogen phosphate with a molar ratio of potassium dihydrogenphosphate relative to hydrogen peroxide comprised in the feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1; and
optionally the propane, preferably in an amount in the range of from 95 to 100%, preferably from 98 to 100%, more preferably from 99 to 100% of the amount contained in the liquid feed stream provided in (i);
the at least one component B in an amount of from 0.01 to 3 weight-%, preferably from 0.015 to 2 weight-%, more preferably from 0.02 to 1 weight-% based on the total weight of the effluent stream.

Preferably, at least 95 weight-%, preferably from 95 to 100 weight-%, more preferably from 98 to 100 weight-% of the effluent stream removed in (iii) consist of propylene oxide, acetonitrile, water, potassium dihydrogen phosphate, the at least one component B, optionally propene, and optionally propane.

Preferably, the effluent stream removed in (iii) comprises potassium with a molar ratio of potassium relative to hydrogen peroxide comprised in the feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1.

According to the present invention, it was found that a concentration of the dissolved potassium dihydrogen phosphate in the liquid feed stream provided in (i) of at least 10%, preferably in the range of from 10 to 100%, preferably from 20 to 100%, more preferably from 30 to 100%, more preferably from 40 to 100%, of the solubility limit of the potassium dihydrogen phosphate in the liquid feed stream allows for an excellent propylene oxide selectivity of the epoxidation reaction in (ii) which is typically at least 90%, preferably at least 93%. More preferably, the propylene oxide selectivity of the epoxidation reaction in (ii) is at least 95%, more preferably at least 96%, more preferably at least 97%, wherein the propylene oxide selectivity is defined as the molar amount of propylene oxide comprised in the effluent stream removed in (iii) relative to the molar amount of hydrogen peroxide comprised in the liquid feed stream provided in (i). Preferably at concentrations of the dissolved potassium dihydrogen phosphate in the liquid feed stream provided in (i) of at least 20%, more preferably at least 25%, more preferably at least 30%, more preferably at least 35%, more preferably at least 40% of the solubility limit of the potassium dihydrogen phosphate in the liquid feed stream, such high propylene oxide selectivities can be achieved, and even selectivities of at least 98% or at least 98.5% can be obtained, wherein in each case, these high selectivities are obtained based on a very high hydrogen peroxide conversion of from 85 to 100%, preferably from 90 to 100% such as from 95 to 100%. These extremely advantageous characteristics were found to be especially pronounced if, as the catalyst comprising a titanium zeolite of framework structure type MWW catalyst in (ii), ZnTiMWW is employed.

Yet further, it was found that in particular if, as the catalyst comprising a titanium zeolite of framework structure type MWW catalyst in (ii), ZnTiMWW is employed, extremely long times on stream of, for example, more than 720 hours such as 1000 hours or more, 1500 hours or more, or 2000 hours or more can be realized wherein the catalyst is subject to essentially no deactivation. In addition to the characteristics described above with regard to the propylene oxide selectivities and hydrogen peroxide conversions, these extremely long times on stream represent a very important process characteristic in view of an economically and ecologically desirable industrial-scale process for the epoxidation of propene.

Still further, it was found that not only the propylene oxide selectivities are very high. At the same time, the selectivities with regard to the most important by-products and side-products of the epoxidation reaction such as oxygen, organic peroxides ROOH and diols are extremely low and can be even decreased if the concentration of the dissolved potassium dihydrogen phosphate in the liquid feed stream provided in (i) is at least 20%, preferably at least 25%, more preferably at least 30%, more preferably at least 35%, more preferably at least 40% of the solubility limit of the potassium dihydrogen phosphate in the liquid feed stream. Further preferred concentrations of the dissolved potassium dihydrogen phosphate in the liquid feed stream provided in (i) are at least 50%, more preferably at least 60%, more preferably at least 70%, more preferably at least 80% of the solubility limit of the potassium dihydrogen phosphate in the liquid feed stream.

Further Downstream Stages

From the effluent stream removed according to (iii), propylene oxide can be separated according to any conceivable method. Preferably, the effluent stream removed in (iii) comprises propene and optionally propane, and the process of the present invention, in addition to steps (i), (ii), and (iii), further comprises (iv) separating propene, optionally together with propane, and oxygen which is optionally additionally contained in the effluent stream, from the effluent stream, obtaining a stream S01 enriched in propylene oxide, acetonitrile, and water, wherein preferably at least 99 weight-% of S01 consist of acetonitrile, water, and propylene oxide; wherein for separation, preferably a fractionation unit is used, wherein preferably, at the top of the fractionation unit, liquid acetonitrile, optionally admixed with liquid water, is added as entraining agent, and wherein S01 is preferably obtained as bottoms streams;

(v) separating propylene oxide from S01, obtaining a top stream comprising propylene oxide and being depleted of acetonitrile and water.

Preferably, prior to (iv), the effluent stream is subjected to a suitable pressure release stage and passed to the separation stage according to (iv). Optionally, the possibly formed gaseous and liquid phases are suitably separated and passed to different trays of the distillation tower employed according to (iv) if the separation according to (iv) is carried via distillation. Alternatively, the effluent stream can be subjected to said pressure release directly in the distillation column employed according to (iv); in this case, no pressure release apparatus downstream of the epoxidation stage and upstream of the separation stage according to (iv) would be necessary. Optionally, the temperature of the effluent stream can be suitably adjusted prior to (iv), preferably after the pressure release stage.

Preferably, in (v), a further stream S02 is obtained, preferably as bottoms stream, which is enriched in acetonitrile and water. Preferably, at least 95 weight-% of S02 consist of acetonitrile and water, wherein more preferably, the weight ratio of acetonitrile relative to water in the stream S02 is greater than 1:1. Therefore, the present invention relates to the process as described above, which comprises (v) separating propylene oxide from S01, obtaining a top stream comprising propylene oxide and being depleted of acetonitrile and water, and obtaining a stream S02, preferably as bottoms stream, enriched in acetonitrile and water, wherein at least 95 weight-% of S02 consist of acetonitrile and water, and wherein the weight ratio of acetonitrile relative to water is greater than 1:1.

Further, the present invention relates to a process comprising (iv) separating propene, optionally together with propane, and oxygen which is optionally additionally contained in the effluent stream, from the effluent stream, obtaining a stream S01 enriched in propylene oxide, acetonitrile, water, and optionally the at least one component B, wherein preferably at least 99 weight-% of S01 consist of acetonitrile, water, preferably the at least one component B, and propylene oxide; wherein for separation, preferably a fractionation unit is used, wherein preferably, at the top of the fractionation unit, liquid acetonitrile, optionally admixed with liquid water, is added as entraining agent, and wherein S01 is preferably obtained as bottoms streams;

(v) separating propylene oxide from S01, obtaining a top stream comprising propylene oxide and being depleted of acetonitrile and water, and obtaining a stream S02, preferably as bottoms stream, enriched in acetonitrile, water and optionally the at least one component B, wherein preferably at least 95 weight-% of S02 consist of acetonitrile, water and preferably the at least one component B, and wherein the weight ratio of acetonitrile relative to water is greater than 1:1.

Regarding step (iv), no specific restrictions exist. Preferably, the separation is carried out so that at least 90 weight-%, more preferably at least 95 weight-%, more preferably at least 98 weight-%, more preferably at least 99 weight-% of S01 consist of acetonitrile, water, preferably the at least one component B, and propylene oxide. Preferably, a fractionation unit is employed for the separation in (iv). Further preferably, the separation in (iv) is carried out in at least one distillation tower, more preferably in one distillation tower. From this distillation tower, S01 is preferably obtained as bottoms stream. Preferably, this distillation tower has from 10 to 30, more preferably from 15 to 25 theoretical trays. The distillation tower is preferably operated at a top pressure of from 0.5 to 1.2 bar, more preferably of from 0.7 to 1.1 bar. In order to facilitate said separation task, it was found that it is advantageous to add either liquid acetonitrile or a liquid mixture of acetonitrile with water to the top of the column. It is believed that this external reflux serves as entraining agent which, among others, prevents propylene oxide from being separated via the top of the distillation tower. According to a preferred embodiment of the present invention, a portion of the bottom stream of the distillation tower preferably employed in stage (v) is used. It is also conceivable that the stream TL2 described hereinbelow or a portion thereof is used as entraining agent. The amount of TL2 will not be sufficient, and another stream is to be added. Preferably, the weight ratio of the amount of acetonitrile fed as external reflux to the top of the distillation tower relative to the weight of the effluent stream removed in (iii) fed into the distillation tower and to be separated in the distillation tower is in the range of from 1:1 to 4:1 preferably from 1.5:1 to 3:1. The temperature of the external reflux is generally in the range of from 2 to 20° C., preferably in the range of from 5 to 15° C. According to the present invention, preferably at least 85 volume-%, more preferably at least 90 volume-%, more preferably at least 93 volume-% of the top stream of the distillation column according to (iv) consist of propene, oxygen, and optionally propane. Depending on its oxygen content, this top stream can be passed to a further suitable work-up stage wherein the oxygen content is suitably decreased in order to allow, e.g., for recycling the oxygen-depleted stream to be recycled to one or more stages of the present invention, such as a starting material for step (ii) of the inventive process like stage (ii-1) or stage (ii-3), or as portion of the stream P described hereinbelow. If the oxygen content of said top stream is reduced, it is preferred to reduce the oxygen by reaction with hydrogen in the presence of a suitable catalyst. For example, it is possible to use catalysts comprising copper in elemental and/or oxidic form on a support, wherein copper is present on the support in an amount of 30 to 80 weight-% based on the whole catalyst and calculated as CuO. Such catalysts can be prepared, for example, according to the example of EP 0 427 062 A2, catalyst 2, page 4, lines 41 to 50 (corresponding to U.S. Pat. No. 5,194,675). In order to reduce the oxygen content, also other suitable methods are conceivable. Optionally, said top stream, prior to be subjected to hydrogenation, can be compressed and partially condensed wherein a liquid stream is obtained which essentially consists of propene and optionally propane and acetonitrile and which contains minor amounts of water. The non-condensed portion essentially consists of propene and optionally propane and oxygen and contains a minor amount of water wherein, compared to the basic stream, the oxygen content is increased while still being in a range so that the mixture is not ignitable. This oxygen-enriched stream is then subjected to hydrogenation.

Regarding step (v), no specific restrictions exist. Preferably, the separation is carried out so that preferably at least 90 weight-%, more preferably at least 95 weight-%, more preferably at least 99 weight-% of S02 consist of acetonitrile, water and optionally the at least one component B. More preferably, the weight ratio of acetonitrile relative to water in S02 is greater than 1:1, preferably in the range of from 2:1 to $10^{-6}$:1, more preferably from 2.5:1 to 5:1. Preferably, a fractionation unit is employed for the separation in (v). Further preferably, the separation in (v) is carried out in at least one distillation tower, more preferably in one distillation tower. Preferably, this tower has of from 50 to 80, more preferably of from 60 to 70 theoretical trays. The distillation tower is preferably operated at a top pressure of from 0.2 to 2 bar, more preferably of from 0.4 to 1 bar. Optionally, at least one suitable polar solvent or a mixture of two or more polar solvents, preferably water, can be added in the upper part of the column as extracting agent.

According to an embodiment of the process of the present invention, the separation according to step (v) can be carried out by
  introducing S01 into an extractive distillation column;
  additionally introducing a polar extracting solvent or a mixture of two or more thereof, preferably water, into said extractive distillation column;
  distilling propylene oxide overhead from said extractive distillation column as top stream, wherein the top stream comprises only minor amounts of acetonitrile such as 500 ppm or less;
  compressing said top stream obtained overhead in the previous step by means of at least one compressor to give a compressed vapor;
  condensing the compressed vapor obtained in the previous step and returning at least part of the heat of condensation to at least one reboiler employed in the extractive distillation column.

From this distillation tower according to (v), a top stream is obtained which contains preferably at least 90 weight-%, more preferably at least 95 weight-%, more preferably at least 99 weight-% of propylene oxide. Further from this distillation tower, S02 is preferably obtained as bottoms stream which preferably contains 500 weight-ppm at most, preferably 100 weight-ppm at most, and more preferably 60 weight-ppm at most of propylene oxide, based on the weight of S02. Depending on the requirements on the propylene oxide quality, it is conceivable to use this propylene oxide fraction without any further purification. It is, however, also conceivable to further purify said propylene oxide fraction, for example in at least one further distillation stage.

From the distillation tower according to (v) or optionally from the further distillation stage, a propylene oxide stream is obtained wherein preferably at least 99.990 weight-%, more preferably at least 99.995 weight-%, more preferably at least 99.999 weight-% of said stream consist of propylene oxide.

Therefore, the present invention also relates to a composition comprising at least 99.990 weight-%, preferably at least 99.995 weight-%, more preferably at least 99.999 weight-% of propylene oxide, preferably obtainable or obtained by a process comprising steps (iv) and (v) as described above.

Generally, the stream S02 as described above can be used as acetonitrile recycle stream which can be used for providing the liquid feed stream in (i). Further, it is possible that the stream S02 is subjected to further work-up steps before it is used as acetonitrile recycle stream which is used for providing the liquid feed stream in (i). Preferably, the stream S02 is subjected to the further work-up steps described hereinbelow in the embodiments 1 to 13.

Prior to step (vi) as described below, it is conceivable
(v-01) to subject the stream S02 obtained from step (v) to hydrogenation; and/or
(v-02) to subject the stream obtained from (v) or from (v-01) to distillation to obtain a bottoms stream,
wherein the hydrogenated stream obtained from (v-01) or the bottoms stream obtained from (v-02) is subjected to further work-up as stream S1. If steps (v-01) and/or (v-02) is/are carried out, it is preferred
(v-01) to subject the stream S02 obtained from (v) to a catalytical hydrogenation stage, the catalyst preferably being a heterogeneous catalysts comprising Ru, Ni, Pd, Pt, either individually or as a mixture of two or more thereof, as active metal on a suitable support material, in particular Pd on activated carbon; said hydrogenation preferably being carried out at a pressure during hydrogenation in the range of from 1 to 100 bar(abs), preferably from 1 to 10 bar(abs), and a temperature during hydrogenation in the range of from 0 to 180° C., preferably from 25 to 120° C., more preferably from 65 to 85° C.; and/or
(v-02) to subject the stream obtained from (v) or from (v-01) to a distillation stage, preferably carried out in a distillation column operated at a top pressure of from 0.7 to 2 bar, more preferably of from 1.1 to 2 bar.

Preferably, the process of the present invention neither comprises (v-01) nor (v-02).

Further Work-Up Steps

Preferably, in particular if the liquid feed stream provided in (i) comprises the at least one component B, the further work-up stages are carried out by a process whose preferred steps and conditions are defined by the following embodiments 1 to 13 and the respective combinations of embodiments resulting from the dependencies as indicated:

1. (vi) dividing S1 into two streams S2 and S3, wherein the total weight of S3 relative to the total weight of S1 is in the range of from 0.01 to 25%;
   (vii) subjecting S3 to a vapor-liquid fractionation in a fractionation unit, obtaining a vapor fraction stream S4 being depleted of the at least one component B, and obtaining a liquid bottoms stream S4b being depleted of acetonitrile;

(viii) recycling at least a portion of S4, optionally after work-up, to (i).
2. The process of embodiment 1, wherein in (vi), the total weight of S3 relative to the total weight of S1 is in the range of from 0.05 to 20%, preferably from 0.1 to 15%, more preferably from 0.2 to 10%, more preferably from 0.5 to 5%.
3. The process of embodiment 1 or 2, wherein from 90 to 99.9 weight-%, preferably from 95 to 99.8 weight-%, more preferably from 99 to 99.7 weight-% of S1 consist of acetonitrile and water and wherein preferably from 0.01 to 5 weight-%, more preferably from 0.015 to 3 weight-%, more preferably from 0.02 to 2 weight-% of S1 consist of the at least one component B.
4. The process of any of embodiments 1 to 3, wherein in (vii), vapor-liquid fractionation is carried out in the fractionation unit so that from 10 to 30 weight-%, preferably from 10 to 25 weight-% of the liquid bottoms stream S4b consist of acetonitrile and from 0.1 to 10 weight-%, preferably from 0.25 to 5 weight-% of the liquid bottoms stream S4b consist of the at least one further component B.
5. The process of any of embodiments 1 to 4, wherein in (vii), vapor-liquid fractionation is carried out in the fractionation unit at an absolute pressure in the range of from 0.1 to 10 bar, preferably from 0.5 to 5 bar, more preferably from 1 to 2 bar.
6. The process of any of embodiments 1 to 5, wherein in (vii), the number of theoretical trays of the fractionation unit is in the range of from 1 to 100, preferably from 2 to 25, more preferably from 3 to 10.
7. The process of any of embodiments 1 to 6, wherein a fraction of S4 is used after condensation as reflux, the reflux ratio preferably being in the range of from 0.01:1 to $10^{-6}$:1, more preferably from 0.1:1 to 5:1, more preferably from 0.5:1 to 2:1.
8. The process of any of embodiments 1 to 6, wherein the fractionation unit is operated without reflux and S3 is fed to the top of the fractionation unit.
9. The process of any of embodiments 1 to 8, wherein from 95 to 99.99 weight-%, preferably from 97 to 99.9 weight-%, more preferably from 98 to 99.9 weight-% of S4 consist of acetonitrile and water, and wherein preferably from 0.0001 to 0.2 weight-%, more preferably from 0.001 to 0.15 weight-%, more preferably from 0.005 to 0.1 weight-% of S4 consist of the at least one component B.
10. The process of any of embodiments 1 to 9, wherein (viii) comprises recycling at least a portion of S4, optionally after work-up, to (i), and recycling at least a portion of S2, optionally after work-up, to step (i).

According to the present invention, the effluent stream removed according to (iii) comprises at least a portion of the potassium dihydrogen phosphate comprised in the feed stream provided in (i). Preferably, the propylene oxide is separated from the effluent stream in one or more suitable stages described hereinabove. Further preferably, the thus obtained stream depleted of propylene oxide is subjected to one or more further stages from which an acetonitrile recycle stream is preferably obtained which is fed back to the epoxidation reaction. A preferred recycling method comprising a stage (viii) is described hereinabove. Preferably, at least a portion of the potassium dihydrogen phosphate comprised in the effluent stream according to (iii) and preferably comprised in the stream S4, more preferably in the streams S4 and S2, is suitably separated from the recycle stream(s) during work-up of S2 and/or S4. More preferably, at least 99%, preferably at least 99.9%, more preferably at least 99.99% of the potassium dihydrogen phosphate comprised in S4, preferably comprised in the streams S4 and S2, are separated from the recycle stream(s) during work-up of S2 and/or S4. Therefore, it is especially preferred that an accumulation of the potassium dihydrogen phosphate caused by a re-use of the recycle stream(s) in (i) is essentially completely prevented.

The Catalytic System

According to the present invention, it was found that the specific combination of a titanium zeolite of framework structure type MWW which optionally comprises zinc, and potassium dihydrogen phosphate which is employed as additive leads to unexpected and superior characteristics of the epoxidation reaction where propylene oxide is prepared from propene, preferably with hydrogen peroxide as epoxidation agent, and preferably in the presence of acetonitrile as solvent. Therefore, the present invention also relates to a catalytic system comprising a catalyst comprising a titanium zeolite of structure type MWW optionally comprising zinc, and potassium dihydrogen phosphate. The term "catalytic system as used in this context of the present invention relates to the system comprised of catalyst comprising a titanium zeolite of structure type MWW optionally comprising zinc, and the potassium dihydrogen phosphate which catalytic system ie realized when the liquid feed provided in (i) is brought in contact with the catalyst in (ii). This catalytic system is characterized by the following embodiments and combinations of embodiments resulting from the dependencies as indicated:

1. A catalytic system comprising a catalyst comprising a titanium zeolite of structure type MWW optionally comprising zinc, and potassium dihydrogen phosphate.
2. The catalytic system of embodiment 1, wherein the titanium zeolite of structure type MWW optionally comprising zinc which is comprised in the catalyst in (ii) contains titanium, calculated as elemental titanium, in an amount in the range of from 0.1 to 5 weight-%, preferably from 1 to 2 weight-%, based on the total weight of the titanium zeolite of framework structure type MWW optionally comprising zinc, and optionally contains zinc, calculated as elemental zinc, in an amount in the range of from 0.1 to 5 weight-%, preferably from 1 to 2 weight-%, based on the total weight of the titanium zeolite of framework structure type MWW optionally comprising zinc.
3. The catalytic system of embodiment 1 or 2, wherein the catalyst comprising a titanium zeolite of framework structure type MWW is a fixed-bed catalyst.
4. The catalytic system of any of embodiments 1 to 3, wherein the catalyst comprising a titanium zeolite of framework structure type MWW comprises zinc and is in the form of a molding, the molding being characterized by the following embodiments and combination of embodiments resulting from the dependencies as indicated:
  4.1 A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.

4.2 The molding of embodiment 4.1, comprising mesopores having an average pore diameter in the range of from 4 to 40 nm, preferably from 20 to 30 nm as determined by Hg porosimetry according to DIN 66133.

4.3 The molding of embodiment 4.1 or 4.2, having a crystallinity, as determined by XRD analysis, of at least (55+/−10) %, preferably in the range of from ((55 to 75)+/−10) %. The crystallinity is understood as being determined according to Reference Example 4.7 of the present invention.

4.4 The molding of any of embodiments 4.1 to 4.3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 4.2 of the present invention.

4.5 The molding of any of embodiments 4.1 to 4.4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 4.3 of the present invention.

4.6 The molding of any of embodiments 4.1 to 4.5, the $^{29}$Si-NMR spectrum of said molding comprising six peaks at the following position
peak 1 at −98+/−x ppm,
peak 2 at −104+/−x ppm,
peak 3 at −110+/−x ppm,
peak 4 at −113+/−x ppm,
peak 5 at −115+/−x ppm,
peak 6 at −118+/−x ppm,
with x in any of the peaks being 1.5, preferably 1.0, more preferably 0.5, wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3. These $^{29}$Si-NMR characteristics are understood as being determined according the Reference Example 4.4 of the present invention.

4.7 The molding of any of embodiments 4.1 to 4.6, having a water uptake in the range of from 3 to 8 weight-%, preferably from 4 to 7 weight-%. The water uptake is understood as being determined according to Reference Example 4.5 of the present invention.

4.8 The molding of any of embodiments 4.1 to 4.7, the infrared spectrum of said molding comprising a band in the region of (3700-3750)+/−20 $cm^{-1}$ and a band in the region of (3670-3690)+/−20 $cm^{-1}$, wherein the intensity ratio of the band in the region of (3700-3750)+/−20 $cm^{-1}$ relative to the band in the region of (3670-3690)+/−20 $cm^{-1}$ is at most 1.5, preferably at most 1.4.

5. The catalytic system of any of embodiments 1 to 4 for the epoxidation of propene.

6. The catalytic system of any of embodiments 1 to 5, being obtainable or obtained by
   (i') providing a liquid feed stream comprising propene, hydrogen peroxide, acetonitrile, water, optionally propane, and dissolved potassium dihydrogen phosphate;
   (ii') passing the liquid feed stream provided in (i') into an epoxidation reactor comprising the catalyst comprising a titanium zeolite of structure type MWW optionally comprising zinc, wherein in (ii'), the liquid feed stream is preferably subjected to epoxidation reaction conditions in the epoxidation reactor, obtaining a reaction mixture comprising propylene oxide, acetonitrile, water, potassium dihydrogen phosphate, optionally propene, and optionally propane.
   wherein the concentration of the dissolved potassium dihydrogen phosphate in the liquid feed stream provided in (i') is at least 10%, preferably in the range of from 10 to 100%, more preferably from 20 to 100%, more preferably from 30 to 100%, more preferably from 40 to 100%, more preferably from 50 to 100%, more preferably from 60 to 100%, more preferably from 70 to 100%, more preferably from 80 to 100%, of the solubility limit of the potassium dihydrogen phosphate in the liquid feed stream.

7. The catalytic system of embodiment 6, wherein the liquid feed stream provided in (i') comprises
   the acetonitrile in amount of from 60 to 75 weight-%, preferably from 60 to 65 weight-%, based on the total weight of the liquid feed stream;
   the hydrogen peroxide in an amount of from 6 to 10 weight-%, preferably from 7 to 9 weight-%, based on the total weight of the liquid feed stream;
   the water in a molar ratio of water relative to acetonitrile of at most 1:4, preferably in the range of from 1:50 to 1:4, preferably from 1:15 to 1:4, more preferably from 1:10 to 1:4.2;
   the propene with a molar ratio of propene relative to hydrogen peroxide comprised in the liquid feed stream in the range of from 1:1 to 1.5:1, preferably from 1.1:1 to 1.4:1;
   the dissolved potassium dihydrogen phosphate with a molar ratio of potassium dihydrogen phosphate relative to hydrogen peroxide comprised in the liquid feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1; and
   optionally the propane with a molar ratio of propane relative to the sum of propene and propane in the range of from 0.0001:1 to 0.15:1, preferably from 0.001:1 to 0.05:1.

8. The catalytic system of embodiment 6 or 7, wherein the liquid feed stream provided in (i') comprises potassium with a molar ratio of potassium relative to hydrogen peroxide comprised in the liquid feed stream in the range of from $25 \times 10^{-6}$:1 to $1000 \times 10^{-6}$:1, preferably from $50 \times 10^{-6}$:1 to $975 \times 10^{-6}$:1, more preferably from $100 \times 10^{-6}$:1 to $950 \times 10^{-6}$:1.

9. The catalytic system of any of embodiments 6 to 8, wherein the liquid feed stream provided in (i') contains ammonium $NH_4^+$ in amount of at most 2 weight-ppm, preferably at most 1 weight-ppm.

10. The catalytic system of any of embodiments 6 to 9, wherein the liquid feed stream provided in (i') contains sodium in a molar ratio of sodium relative to hydrogen peroxide in the range of from $1 \times 10^{-6}$:1 to $250 \times 10^{-6}$:1, preferably from $5 \times 10^{-6}$:1 to $50 \times 10^{-6}$:1.

11. The catalytic system of any of embodiments 6 to 10, wherein the liquid feed stream passed into the reactor in (ii') has a temperature in the range of from 0 to 60° C., preferably from 25 to 50° C., and is at a pressure in the range of from 14 to 100 bar, preferably from 15 to 25 bar.
12. The catalytic system of any of embodiments 6 to 11, wherein in (ii'), the temperature of the reaction mixture is controlled using a heat transfer medium, preferably by passing the heat transfer medium through a jacket of the epoxidation reactor.
13. The catalytic system of any of embodiments 6 to 12, wherein in (ii'), the epoxidation conditions comprise an epoxidation reaction temperature in the range of from 20 to 100° C., preferably from 30 to 80° C., more preferably from 40 to 60° C., wherein the epoxidation reaction temperature is defined as the temperature of the heat transfer medium prior to controlling of the temperature of the reaction mixture, preferably as the temperature of the heat transfer medium at the entrance of the jacket of the epoxidation reactor
14. The catalytic system of any of embodiments 6 to 13, wherein in (ii'), the epoxidation conditions comprise an epoxidation reaction pressure in the range of from 14 to 100 bar, preferably from 15 to 32 bar, more preferably from 15 to 25 bar, wherein the epoxidation reaction pressure is defined as the pressure at the exit of the epoxidation reactor.
15. The catalytic system of any of embodiments 6 to 14, wherein in (ii'), the reaction mixture is liquid under the epoxidation conditions, the reaction mixture preferably consisting of one single liquid phase under the epoxidation conditions.
16. The catalytic system of any of embodiments 6 to 15, having a deactivation rate of at most 0.010 K/d, preferably at most 0.005 K/d, at a concentration of the dissolved potassium dihydrogen phosphate in the liquid feed stream provided in (i) in the range of from 70 to 100%, preferably from 80 to 100% of the solubility limit of the potassium dihydrogen phosphate in the liquid feed stream provided in (i).

Yet further, the present invention relates to the use of potassium dihydrogen phosphate as an additive for a titanium zeolite of framework structure type MWW optionally comprising zinc in a preferably continuous process for the preparation of propylene oxide, preferably in acetonitrile as solvent, and preferably with hydrogen peroxide as epoxidation agent.

The present invention is further illustrated by the following reference examples, examples and comparative examples.

EXAMPLES

Reference Example 1: Epoxidation Reaction Setup

A vertically arranged tubular reactor (length: 1.4 m, internal diameter: 7 mm) equipped with a jacket for thermostatization was charged with 15 g of the respective catalyst in the form of strands with a diameter of 1.5 mm as described in Reference Example 2 and Reference Example 3 below. The remaining reactor volume was filled with inert material (steatite spheres, 2 mm in diameter) to a height of about 5 cm at the lower end of the reactor and the remainder at the top end of the reactor.

The reactor was thermostatized by passing a mixture of water and ethylene glycol as heat transfer medium through the jacket. The heat transfer medium was fed at the lower end of the jacket, flowing in co-current mode relative to the liquid feed stream passed into the reactor. The temperature of the heat transfer medium at the entrance of the jacket was defined as the reaction temperature, also referred to as $T_r$. The flow rate of the heat transfer medium was suitably adjusted so that the difference between its temperature at the entrance of the jacket and its temperature at the exit of the jacket was at most 1 K.

The pressure in the reactor was controlled by a pressure control valve and maintained at a constant value of 20 $bar_{abs}$.

The reactor feed stream was combined from three separate feed streams which were metered by using separate metering pumps:
 The first stream consisted either of acetonitrile (Asahi Kasei, chemical grade, acetonitrile content at least 99.9 weight-%, water content less than 500 weight-ppm) or, depending on the desired reaction conditions, of an acetonitrile/water mixture. This first stream was employed having a flow rate of 68 g/h.
 The second stream consisted of liquefied polymer grade propene, having a propane content of 99.5 weight-%. This second stream was employed having a flow rate of 10.8 g/h.
 The third stream consisted of an aqueous hydrogen peroxide solution with a hydrogen peroxide concentration of 40 weight-%. This third stream was employed having a flow rate of 16.8 g/h. Potassium dihydrogen phosphate used in the experiments as additive was dissolved in the hydrogen peroxide stream in amounts shown below in the examples.

The three feed streams were premixed before the mixed feed was fed at ambient temperature to the bottom of the tubular reactor as liquid feed stream. Under the conditions the liquid feed stream consisted of one single liquid phase.

The experiments were performed in a continuous manner. At the start of the run (t=0, defined as the point in time at which the hydrogen peroxide metering pump was started), the reaction temperature was set to a value in the range of 30 to 45° C. as shown in the examples. With a fresh catalyst this resulted in an initial 100% conversion of hydrogen peroxide. After a certain period of time, usually within 100 hours on stream, the hydrogen peroxide conversion started to decrease. The temperature was then adjusted, generally once to twice a day, in order to keep the hydrogen peroxide conversion in a range of from 85 to 96%. The average rate at which the temperature was increased in order to keep the hydrogen peroxide conversion essentially constant, referred to hereinbelow as the parameter delta $T_r$/delta t, is a measure of the rate of catalyst deactivation. This parameter was calculated by dividing the difference between the cooling medium temperature at end of the indicated time period and the starting temperature and dividing it by the total number of hours on stream.

The reactor effluent stream downstream the pressure control valve was collected, weighed and analyzed. Organic components, with the exception of hydroperoxypropanols and oxygen were analyzed in two separate gas-chromatographs. The hydrogen peroxide content was determined colorimetrically using the titanyl sulfate method. The content of hydroperoxypropanols, a mixture of 1-hydroperoxypropanol-2 and 2-hydroperoxypropanol-1, was determined by iodometrically measuring the total peroxide content and then subtracting the hydrogen peroxide content.

The selectivity for propylene oxide given was determined relative to the hydrogen peroxide and was calculated as 100 times the ratio of moles of propylene oxide in the effluent stream divided by the moles of hydrogen peroxide in the feed. The selectivity for propylene glycol given was calculated as 100 times the ratio of moles of propylene glycol in the effluent divided by the moles of hydrogen peroxide in the feed. The selectivity for hydroperoxypropanols given was calculated as 100 times the ratio of twice the number of moles of hydroperoxypropanols in the effluent divided by the moles of hydrogen peroxide in the feed. The selectivity for molecular oxygen given was calculated as 100 times the ratio of twice the number of moles of molecular oxygen in the effluent divided by the moles of hydrogen peroxide in the feed.

Reference Example 2: Preparation of Epoxidation Reaction Catalyst (ZnTiMWW)

2.1 Preparation of Boron Containing Zeolite of Structure MWW (BMWW)

A 2 m³ stirred tank reactor was first loaded with 470.4 kg of deionized water. After starting the stirrer at 70 rpm, boric acid (162.5 kg) was added and the suspension was stirred for 3 h. Subsequently, piperidine (272.5 kg) was added at once causing the temperature to rise from 28° C. to 46° C. To this solution colloidal silica (Ludox AS40, 392.0 kg) was added. The reactor was then slowly heated to 170° C. within 5 hours and then kept at this temperature under stirring for 120 hours. The maximum pressure during the reaction was 9.3 bar. Afterwards the reactor was cooled down to 50° C. The gel obtained had a pH of 11.3 and a viscosity of 15 mPa·s at 20° C. The gel was then filtered and the filter cake washed with deionized water until the conductivity of the washings was below 500 microSiemens/cm. The filter cake was then suspended in deionized water and the suspension was spray-dried at 235° C. using nitrogen as the carrier gas. The white powder obtained (174.3 kg) contained 3.5 weight-% water. This white powder was then calcined at 650° C. in a rotary kiln to give 138.2 kg of boron containing zeolite of structure type MWW (BMWW) as a white powder.

2.2 Deboronation of BMWW with Water

A 5 m³ stirred tank reactor was loaded with 125 kg of the BMWW obtained according to the previous step and 3750 kg of deionized water. The reactor was then slowly heated to 100° C. within 1 hour under stirring at 70 rpm, and then kept at this temperature for 20 hours and finally cooled to a temperature below 50° C. before it was filtered. The filter cake was then washed with deionized water until the washings had conductivity below 15 microSiemens. The filter cake was then dried for 6 hours under a nitrogen stream. The filter cake was then removed and suspended in 850 kg of deionized water. This suspension was then spray-dried at 235° C. using nitrogen as the carrier gas. The spray dried material weighed 118.5 kg and contained 42.5 weight-% Si, 0.06 weight-% B and 0.23 weight-% C (total organic carbon, TOC).

2.3 Preparation of Titanium Containing Zeolite of Structure Type MWW (TiMWW)

A 2 m³ stirred tank reactor was first loaded with 111.2 kg of the spray-dried material from the previous step 2.2. In a separate 2 m³ stirred tank reactor were placed 400 kg of deionized water. After starting the stirrer at 80 rpm, piperidine (244.0 kg) was added. After the addition of piperidine was finished the mixture was stirred for 5 minutes before tetrabutyl orthotitanate (22.4 kg) was added. The pipe through which the titanate was added was then flushed with 40 kg of deionized water. The mixture was then stirred for 1 hour before being added to the first stirred tank reactor containing the spray-dried powder under stirring (50 rpm). The reactor was then heated to 170° C. and kept at this temperature for 120 h before being cooled to 50° C. The maximum pressure during the reaction was 10.6 bar. The cooled suspension was then filtered and the filter cake was washed with deionized water until the washings had conductivity below 1300 microSiemens/cm and an approximately neutral pH value. The filter cake was then dried under a nitrogen stream for 6 hours. The filter cake containing about 80 weight-% of water was used directly for the next step. The filter cake from the previous step and 1000 kg of deionized water were filled in a 2 m³ stirred tank reactor. Then 1900 kg of nitric acid (53 weight-% in water) were added under stirring at 70 rpm. The reactor was then heated to 100° C. and kept at this temperature for 20 hours before being cooled to 50° C. The suspension obtained was then filtered and the filter cake was washed with deionized water until the conductivity was below 10 microSiemens/cm and the washings were approximately neutral. Subsequently the filter cake was dried under a stream of nitrogen for 6 hours. This filter cake was then suspended in water and spray-dried at 235° C. using nitrogen as the carrier gas. 96 kg of a spray-dried powder were obtained. This material was then calcined in a rotary kiln at 650° C. 84 kg of titanium zeolite of structure type MWW (TiMWW) were obtained as a powder containing 43 weight-% Si, 2.0 weight-% Ti and 0.2 weight-% C (TOC). The pore volume determined by Hg-porosimetry according to DIN 66133 was 7.3 ml/g and the BET surface area determined according to DIN 66131 was 467 m²/g.

2.4 Preparation of a Zinc Containing TiMWW (ZnTiMWW) by Impregnation

A 2 m³ stirred tank reactor was then loaded with 960 kg of water and 5.83 kg of zinc acetate dihydrate. After stirring for 30 min, TiMWW powder (32.0 kg, obtained according to the previous step) was added. The reactor was then heated to 100° C. and kept at this temperature for 4 hours before being cooled to 50° C. The suspension obtained was then filtered and the filter cake was washed 5 times with 120 liter portions of deionized water. The washed filter cake was then dried under a stream of nitrogen for 6 hours. It was then suspended in deionized water and spray-dried at 235° C. using nitrogen as the carrier gas. 34 kg of spray-dried material were obtained which was then calcined at 650° C. for 30 min in a rotary kiln. 28.5 kg of TiMWW containing zinc (ZnTiMWW) powder were obtained that contained 42 weight-% Si, 1.9 weight-% Ti, 1.6 weight-% Zn and 0.16 weight-% C (TOC). The pore volume determined by Hg-porosimetry according to DIN 66133 was 6.6 ml/g and the BET surface area determined according to DIN 66131 was 335 m²/g.

2.5 Preparation of Moldings Containing ZnTiMWW and Silica Binder

In a kneader the ZnTiMWW powder from the previous step (27.0 kg) and hydroxymethylcellulose (Walocel™, 2.0 kg) were kneaded for 5 minutes. Then colloidal silica (Ludox® AS 40, 16.9 kg) was added. After kneading for 10 minutes deionized water (57.6 kg) was added and the mixture was kneaded for further 60 minutes. The paste obtained was then extruded through plates with cylindrical holed with 1.5 mm diameter with a pressure of 65-80 bar. The strands obtained were dried for 16 hours at 120° C. and then calcined for 5 hours at 500° C. The strands obtained were then sieved in a 0.8 mm sieve to remove fines. The ZnTiMWW catalyst strands obtained (34.2 kg) had a diameter of 1.5 mm and lengths between 5 and 25 mm. The bulk density of the catalyst was 345 g/l. The pore volume determined by Hg-porosimetry determined according to DIN 66133 was 1.1 ml/g and the BET surface area determined according to DIN 66131 was 371 m²/g. The elementary analysis showed that the molded ZnTiMWW catalyst contained 41 weight-% Si, 1.4 weight-% Ti and 1.2 weight-% Zn.

Reference Example 3: Preparation of Epoxidation Reaction Catalyst (TiMWW)

3.1 Preparation of Boron Containing Zeolite of Structure MWW (BMWW)

A 50 liter stirred tank reactor was loaded with 22.05 kg of deionized water and 8.515 kg of piperidine. The mixture was then stirred for a few minutes at 150 rpm before 5.076 kg of boric acid were added. The resulting mixture was stirred for 30 minutes. Pyrogenic silica (Aerosil 200, 4.9 kg) was then added portion wise and the resulting suspension was stirred for 2 hours. The reactor was then heated to 170° C. within 2 hours and kept at this temperature for 120 hours. The maximum pressure during the reaction was 8.9 bar. After cooling to 50° C. the suspension was filtered and the filter cake was washed twice, each washing using 50 liters of deionized water. The filter cake was then dried for 24 hours at 80° C. under a stream of nitrogen, then oven-dried at 100° C. for 16 hours and finally calcined at 600° C. for 10 hours to obtain 4.95 kg of a white BMWW powder containing 1.4 weight-% B.

3.2 Deboronation of BMWW with Acid

A 200 liter stirred tank reactor was loaded with 150 kg of nitric acid (30 weight-% in water) and the BMWW powder from the previous step and stirred at 100 rpm for 10 minutes. The reactor was then heated to 100° C. and kept at this temperature under stirring for 20 hours. After cooling to 50° C. the suspension was filtered and the filter cake washed with deionized water until the washings were approximately neutral. The filter cake was then dried for 15 hours under a stream of nitrogen and finally oven dried at 120° C. for 16 hours. 4.117 kg of a white powder containing 0.061 weight-% B were obtained.

3.3 Preparation of Titanium Containing Zeolite of Structure Type MWW (TiMWW)

A 20 liter stirred tank reactor was then loaded with 10.5 kg of deionized water and 5.07 kg of piperidine. The mixture was stirred (170 rpm) for 10 minutes before adding 700 g of tetrabutyl orthotitanate. The mixture was stirred for a further 30 min and then 3.5 kg of the powder obtained from the previous step 3.2 were added. After stirring for 2 hours the reactors was heated to 170° C. and kept at this temperature for 120 hours. The maximum pressure during the reaction was 9.1 bar. After cooling to 50° C. the resulting suspension was filtered and the filter cake was washed with twice with 25 liters of deionized water per washing. The filter cake was then dried at 100° C. for 48 hours. 4.073 kg of a wet white powder containing 2.3 weight-% Ti, 36.0 weight-% Si and 10.4 weight-% C (TOC) were obtained. The powder (4.0 kg) and 120 kg of nitric acid (30 weight-% in water) were then loaded to a 200 liter stirred tank reactor. The suspension was then stirred at 100 rpm and the reactor heated to 100° C. and kept at this temperature for 20 hours. After cooling to 50° C. the resulting suspension was filtered and the filter cake washed with deionized water until the washings were approximately neutral. The filter cake was then dried at 120° C. for 16 hours and finally calcined at 550° C. for 10 hours. 3.185 kg of TiMWW powder with 1.7 weight-% Ti and 45.0 weight % Si were obtained.

3.4 Preparation of Moldings Containing TiMWW and Silica Binder

TiMWW powder (3.0 kg) obtained from the previous step 3.3 and hydroxymethylcellulose (Walocel™, 200 g) were kneaded for 5 minutes. Then colloidal silica (Ludox® AS40, 2.5 kg) were added under continuous kneading. After a further 10 min of kneading deionized water (3.0 kg) was added under kneading. The paste thus obtained was then extruded through plates with cylindrical holed with 1.5 mm diameter with a pressure of 75-85 bar. The strands obtained were dried for 16 hours at 120° C. and then calcined for 5 hours at 500° C. The strands obtained were then sieved using a 0.8 mm sieve to remove fines. The TiMWW catalyst strands obtained (3.88 kg) had a diameter of 1.5 mm and lengths between 5 and 25 mm. The pore volume determined by Hg-porosimetry according to DIN 66133 was 0.7 ml/g and the BET surface area determined according to DIN 66131 was 92 m$^2$/g. The elementary analysis showed that the molded TiMWW catalyst contained 43.5 weight-% Si and 1.1 weight-% Ti.

Reference Example 4: Characterization of the Catalyst

Reference Example 4.1: Determination of Dv10, Dv50, and Dv90 Values 1.0 g of the micropowder is suspended in 100 g deionized water and stirred for 1 min. The sample was subjected to the measurement in an apparatus using the following parameters: Mastersizer S long bed version 2.15, ser. No. 33544-325; supplier: Malvern Instruments GmbH, Herrenberg, Germany: focal width 300RF mm; beam length 10.00 mm; module MS17; shadowing 16.9%; dispersion model 3$$D; analysis model polydisperse correction none.

Reference Example 4.2: Determination of the Silanol Concentration of the Moldings of the Present Invention For the determination of the silanol concentration, the $^{29}$Si MAS NMR experiments were carried out at room temperature on a VARIAN Infinityplus-400 spectrometer using 5.0 mm ZrO$_2$ rotors. The $^{29}$Si MAS NMR spectra were collected at 79.5 MHz using a 1.9 μs π/4 (microsecond pi/4) pulse with 10 s recycle delay and 4000 scans. All $^{29}$Si spectra were recorded on samples spun at 6 kHz, and chemical shifts were referenced to 4,4-dimethyl-4-silapentane sulfonate sodium (DSS). For the determination of the silanol group concentration, a given $^{29}$Si MAS NMR spectrum is deconvolved by the proper Gaussian-Lorentzian line shapes. The concentration of the silanol groups with respect to the total number of Si atoms is obtained by integrating the deconvolved $^{29}$Si MAS NMR spectra.

Reference Example 4.3: Determination of the Crush Strength of the Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 4.4: $^{29}$Si Solid-State NMR Spectra Regarding $Q^3$ and $Q^4$ Structures The effect of the inventive water treatment on the molding related to $Q^3$ and $Q^4$ structures in the material was characterized by comparing the changes in $^{29}$Si solid-state NMR spectra under comparable conditions. All $^{29}$Si solid-state NMR experiments were performed using a Bruker Advance spectrometer with 300 MHz $^1$H Larmor frequency (Bruker Biospin, Germany). Samples were packed in 7 mm $ZrO_2$ rotors, and measured under 5 kHz Magic Angle Spinning at room temperature. $^{29}$Si direct polarization spectra were obtained using (pi/2)-pulse excitation with 5 microsecond pulse width, a $^{29}$Si carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethyl-silyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula 100*{[$a_1$−$a_2$]/[$a_4$+$a_5$+$a_6$]}/$a_3$. In this formula, $a_{i, i=1 \ldots 6}$ represents the area of the fitted peak to which this number was attributed.

Reference Example 4.5: Water Adsorption/Desorption—Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 wt. %). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 wt. % from 5 to 85% and at each step the system controlled the RH and monitored the sample weight until reaching the equilibrium conditions and recording the weight uptake. The total adsorbed water amount by the sample was taken after the sample was exposed to the 85 weight-% RH. During the desorption measurement the RH was decreased from 85 wt. % to 5 wt. % with a step of 10% and the change in the weight of the sample (water uptake) was monitored and recorded.

Reference Example 4.6: FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 cm region were analyzed and for comparing multiple samples, as reference the band at 1880±5 $cm^{-1}$ was taken.

Reference Example 4.7: Determination of Crystallinity Via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm.

The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

Reference Example 5: Definition and Determination of the Octanol-Water Partition Coefficient $K_{OW}$ The octanol-water partition coefficient $K_{OW}$ of a given compound is defined as the ratio of said compound's chemical concentration in the octanol phase relative to said compound's chemical concentration in the aqueous phase in a two-phase system of 1-octanol and water at a temperature of 25° C. The octanol-water partition coefficient $K_{OW}$ of a given compound is determined using the shake-flask method which consists of dissolving the compound in a volume of high-purity 1-octanol and deionized water (pre-mixed and calibrated for at least 24 h) and measuring the concentration of the compound in each the 1-octanol phase and the water phase by a sufficiently exact method, preferably via UV/VIS spectroscopy. This method is described in the OECD Guideline for the testing of chemicals, number 107, adopted on Jul. 27, 1995.

Example 1: Effect of Increasing Amount of $KH_2PO_4$ Using ZnTiMWW and Chemical Grade Acetonitrile as Solvent Examples 1.1 to 1.7 were performed according to epoxidation reaction setup as described in Reference Example 1 above. The reactor was loaded with the ZnTiMWW catalyst according to Reference Example 2. Chemical grade acetonitrile was used as the solvent. The experiment was run continuously and without interruption for 2206 h. The starting temperature was set to 45° C. In different time periods, as indicted in Table 1 below, hydrogen peroxide streams, the third stream as described in Reference Example 1 above, with respectively different concentrations of $KH_2PO_4$ were employed as indicated in Table 1 below. The concentrations of $KH_2PO_4$ are given in Table 1 below as the potassium concentration in micromol per mol hydrogen peroxide. The solubility limit of $KH_2PO_4$ in the reaction feed used in this example was separately determined as being 650 micromol/mol $H_2O_2$.

TABLE 1

| | | | Results of Examples 1.1 to 1.7 | | | | | | |
|---|---|---|---|---|---|---|---|---|---|
| Ex. | Time on stream/h | $[K^+]$/ µmol/mol ($H_2O_2$) | Conversion $H_2O_2$ at the end of the period/% | $T_r$/ ° C. | delta $T_r$/ delta t/ K/d | Selectivity/% | | | |
| | | | | | | PO [1] | MPG [2] | ROOH [3] | $O_2$ |
| 1.1 | 0-477 | 130 | 90.1 | 53.1 | 0.4 | 96.8 | 0.5 | 1.0 | 1.7 |
| 1.2 *) | 477-645 | 0 | 88.1 | 57.8 | 0.8 | 94.5 | 0.8 | 1.7 | 3.0 |
| 1.3 | 645-791 | 130 | 95.6 | 58.9 | 0.3 | 95.7 | 0.7 | 1.1 | 2.5 |
| 1.4 | 791-1126 | 260 | 93.6 | 53.2 | 0.07 | 97.0 | 0.4 | 0.7 | 2.0 |
| 1.5 | 1126-1295 | 390 | 93.4 | 49.8 | 0.02 | 97.3 | 0.3 | 0.6 | 1.8 |
| 1.6 | 1295-2014 | 520 | 91.5 | 43.2 | <0.005 | 97.8 | 0.1 | 0.5 | 1.6 |
| 1.7 | 2014-2206 | 650 | 91.9 | 43.8 | <0.005 | 97.8 | 0.1 | 0.4 | 1.6 |

[1] propylene oxide
[2] monopropylene glycol
[3] hydroperoxypropanols
*) comparative example These examples 1.1 to 1.7 clearly show that an increase in the amount of the additive $KH_2PO_4$ leads to a steady increase in the propylene oxide selectivity of the epoxidation reaction and to a steady decrease in the selectivities of undesired by-products such as monopropylene glycol, hydroperoxypropanols, and oxygen. Additionally, the increase in the amount of the additive $KH_2PO_4$ leads to a steady increase in the activity of the catalyst which is shown by the decreasing temperature which is necessary to achieve the $H_2O_2$ conversion in the desired range as indicated in Reference Example 1 above. Further, the increase in the amount of the additive $KH_2PO_4$ leads to a steady decrease in the rate of deactivation of the catalyst which is shown by the decrease in the parameter delta $T_r$/delta t.

Example 2: Effect of Increasing Amount of $KH_2PO_4$ Using ZnTiMWW and a Mixture of Acetonitrile and Water as Solvent Examples 2.1 and 22 were carried out as examples 1.1 to 1.7. Instead of chemical grade acetonitrile, a mixture of acetonitrile and water was used as solvent (85 weight-% acetonitrile, 15 weight-% water). The examples 2.1 and 2.2 were performed making using a fresh charge of the ZnTiMWW catalyst according to Reference Example 2. The solubility limit of $KH_2PO_4$ in the reaction feed used in this example was separately determined as being 1,600 micromol/mol $H_2O_2$.

TABLE 2

Results of Examples 2.1 and 2.2

| Ex. | Time on stream/h | [K+]/ μmol/mol ($H_2O_2$) | Conversion $H_2O_2$ at the end of the period/% | $T_r$/ °C. | delta $T_r$/ delta t/ K/d | Selectivity/% | | | |
|---|---|---|---|---|---|---|---|---|---|
| | | | | | | PO [1] | MPG [2] | ROOH [3] | $O_2$ |
| 2.1 | 0-237 | 130 | 90.2 | 51.0 | 0.6 | 96.4 | 0.8 | 1.5 | 1.3 |
| 2.2 | 237-573 | 520 | 91.0 | 47.0 | 0.03 | 97.7 | 0.6 | 0.6 | 1.1 |

[1] propylene oxide
[2] monopropylene glycol
[3] hydroperoxypropanols

In the same way as the examples 1.1 to 1.7, also the examples 2.1 and 2.2 show the positive effect of an increase in the amount of the additive $KH_2PO_4$ on both the propylene oxide selectivity and the by-product selectivities. Further, the positive effect on the activity of the catalyst and the deactivation rate of the catalyst is shown. Therefore, it was shown that the advantageous effects observed according to examples 1.1 to 1.7 are not only achieved for acetonitrile as solvent but also for a mixture of acetonitrile and water as solvent, even for a mixture of acetonitrile and water having a comparatively high water content. This latter independency of the water content of the acetonitrile is in particular an advantage for medium or large scale processes where acetonitrile is worked up downstream the epoxidation stage and recycled into the epoxidation reaction wherein comparatively high amounts of water are recycled together with the acetonitrile.

Example 3: Effect of Increasing Amount of $KH_2PO_4$ Using TiMWW and Chemical Grade Acetonitrile as Solvent Examples 3.1 and 3.2 were carried out as examples 1.1 to 1.7. Instead of the ZnTiMWW catalyst, the TiMWW catalyst prepared according to Reference Example 3 was employed. The starting temperature was set at 30° C. The solubility limit of $KH_2PO_4$ in the reaction feed used in this example was separately determined as being 650 micromol/mol $H_2O_2$.

In the same way as the examples 1.1 to 1.7, and 2.1 and 2.2, also the examples 3.1 and 3.2 show the positive effect of an increase in the amount of the additive $KH_2PO_4$ on both the propylene oxide selectivity and the by-product selectivities. Further, the positive effect on the activity of the catalyst and the deactivation rate of the catalyst is shown. Therefore, it was shown that the advantageous effects observed according to examples 1.1 to 1.7 and 2.1 and 2.2 are not only achieved for a ZnTiMWW catalyst but also for a TiMWW which is not doped with zinc. Further, comparing the results of the examples 2.1 and 2.2 with the results of the examples 3.1 and 3.2, it is shown that the ZnTiMWW catalyst is even more preferred at increasing amounts of additive $KH_2PO_4$.

Example 4: Effect of Increasing Amount of $KH_2PO_4$ Using ZnTiMWW and Chemical Grade Acetonitrile as Solvent with a Lower Acetonitrile Concentration Examples 4.1 to 4.8 were carried out as examples 1.1 to 1.7 but with a reduced feed rate of acetonitrile of only 43.9 g/h. In these examples, the starting temperature was set at 40° C. and the temperature was kept constant at this value throughout the experiment. Instead of increasing the temperature of the cooling medium, the amount of additive used was increased at regular intervals. The solubility limit of $KH_2PO_4$ in the reaction feed used in this example was separately determined as being 1,105 micromol/mol $H_2O_2$.

TABLE 3

Results of Examples 3.1 and 3.2

| Ex. | Time on stream/h | [K+]/ μmol/mol ($H_2O_2$) | Conversion $H_2O_2$ at the end of the period/% | $T_r$/ °C. | delta $T_r$/ delta t/ K/d | Selectivity/% | | | |
|---|---|---|---|---|---|---|---|---|---|
| | | | | | | PO [1] | MPG [2] | ROOH [3] | $O_2$ |
| 3.1 | 0-237 | 130 | 91.9 | 64.5 | 2.3 | 89.6 | 0.9 | 6.0 | 3.5 |
| 3.2 | 237-573 | 520 | 90.2 | 58.3 | 0.005 | 95.3 | 0.6 | 1.8 | 2.6 |

[1] propylene oxide
[2] monopropylene glycol
[3] hydroperoxypropanols

TABLE 4

Results of Examples 4.1 to 4.8

| Ex. | Time on stream/h | [K+]/ μmol/ mol ($H_2O_2$) | Conversion $H_2O_2$ at the end of the period/% | Selectivity/% | | | |
|---|---|---|---|---|---|---|---|
| | | | | PO [1] | MPG [2] | ROOH [3] | $O_2$ |
| 4.1 | 0-429 | 650 | 96.4 | 98.8 | 0.26 | 0.22 | 0.7 |
| 4.2 | 429-875 | 715.5 | 96.4 | 98.7 | 0.23 | 0.18 | 0.8 |
| 4.3 | 857-1025 | 780 | 96.3 | 98.6 | 0.21 | 0.17 | 0.8 |
| 4.4 | 1025-1504 | 845 | 95.9 | 98.7 | 0.18 | 0.17 | 0.9 |
| 4.5 | 1504-1694 | 910 | 96.5 | 98.7 | 0.20 | 0.14 | 0.9 |
| 4.6 | 1694-1861 | 975 | 97.8 | 98.6 | 0.20 | 0.18 | 0.9 |
| 4.7 | 1861-2030 | 1040 | 99.1 | 98.6 | 0.20 | 0.13 | 1.0 |
| 4.8 | 2030-2198 | 1105 | 98.7 | 98.7 | 0.18 | 0.13 | 0.9 |

[1] propylene oxide
[2] monopropylene glycol
[3] hydroperoxypropanols

These examples 4.1 to 4.8 show that in spite of the reduced amount of solvent used the propylene oxide selectivity can be maintained constant without the need of increasing the temperature. In fact, in the course of the experiment even a slight increase of conversion was observed with the highest concentrations of additive and no detrimental effect on the selectivity could be detected at the higher conversion. This once again demonstrates the positive effect of the high amounts of additive.

CITED LITERATURE

WO 2011/006990
WO 2009/008493
US 2007043226 A1
U.S. Pat. No. 6,114,551
Wu et al., "Hydrothermal Synthesis of a novel Titanosilicate with MWW Topology", Chemistry Letters (2000), pp. 774-775
Ullmann's Encyclopedia of Industrial Chemistry, 5$^{th}$ edition, volume A 13 (1989) pp. 443-466
EP 1 122 249 A1
EP 0 427 062 A2
U.S. Pat. No. 5,194,675
WO 2012/074118
WO 2011/152268
US 2003/0187284
Lihao Tang et al., *Macromolecules,* 2008, 41, 7306-7315.

The invention claimed is:

1. A process for preparing propylene oxide, comprising:
  (i) preparing a liquid feed stream comprising propene, hydrogen peroxide, acetonitrile, water, and dissolved potassium dihydrogen phosphate;
  (ii) feeding the liquid feed stream into an epoxidation reactor comprising a catalyst comprising a titanium zeolite of framework structure MWW;
  (iii) subjecting the liquid feed stream to epoxidation reaction conditions in the epoxidation reactor to obtain a reaction mixture comprising propylene oxide, acetonitrile, water, and potassium dihydrogen phosphate;
  (iv) removing the reaction mixture as an effluent stream from the epoxidation reactor; and
  (v) separating the propylene oxide from the effluent stream;
  wherein
  operations (i) to (v) are conducted as a continuous method, and
  in the liquid feed stream:
  a concentration of the dissolved potassium dihydrogen phosphate is at least 10% of a solubility limit of potassium dihydrogen phosphate in the liquid feed stream.

2. The process of claim 1, wherein the concentration of the dissolved potassium dihydrogen phosphate in the liquid feed stream prepared in (i) is from 50 to 100% of the solubility limit of potassium dihydrogen phosphate in the liquid feed stream provided in (i).

3. The process of claim 1, wherein in the liquid feed stream prepared in (i)
  a weight-% of acetonitrile is from 60 to 75 weight-%, based on a total weight of the liquid feed stream;
  a weight-% of hydrogen peroxide is from 6 to 10 weight-%, based on the total weight of the liquid feed stream;
  a molar ratio of water relative to acetonitrile is at most 1:4;
  a molar ratio of propene relative to hydrogen peroxide in the liquid feed stream is from 1:1 to 1.5:1; and
  a molar ratio of potassium dihydrogen phosphate relative to hydrogen peroxide in the liquid feed stream is from $25 \times 10^{-6}:1$ to $1000 \times 10^{-6}:1$;
  wherein at least 95 weight-% of the liquid feed stream prepared in (i) consist of propene, hydrogen peroxide, acetonitrile, water] and the dissolved potassium dihydrogen phosphate.

4. The process of claim 1, wherein the liquid feed stream prepared in (i) further comprises ammonium $NH_4^+$ in an amount of at most 2 weight-ppm and sodium in a molar ratio of sodium relative to hydrogen peroxide of from $1 \times 10^{-6}:1$ to $250 \times 10^{-6}:1$.

5. The process of claim 1,
  wherein in (i), the liquid feed stream is prepared by combining a stream comprising hydrogen peroxide, a stream comprising acetonitrile, and a stream comprising propene,
  wherein an aqueous stream comprising the dissolved potassium dihydrogen phosphate is combined with the stream comprising hydrogen peroxide, or with the stream comprising acetonitrile, or with the stream comprising propene, or with a mixed stream of two or three thereof,
  wherein a hydrogen peroxide concentration in the stream comprising hydrogen peroxide is from 25 to 75 weight-%, based on a total weight of the aqueous hydrogen peroxide stream, and
  the aqueous hydrogen peroxide stream further comprises sodium and a molar ratio of the sodium relative to the hydrogen peroxide is from $1 \times 10^{-6}:1$ to $250 \times 10^{-6}:1$.

6. The process of claim 1, wherein the liquid feed stream fed to the epoxidation reactor in (ii) has a temperature of from 0 to 60° C. and a pressure of from 14 to 100 bar.

7. The process of claim 1, further comprising controlling the temperature of the epoxidation reaction mixture to a temperature of from 20 to 100° C. using a heat transfer medium,
  wherein the epoxidation reaction temperature is defined as the temperature of the heat transfer medium prior to controlling the temperature of the reaction mixture.

8. The process of claim 1, wherein in (ii), an epoxidation reaction pressure is from 14 to 100 bar,
  wherein the epoxidation reaction pressure is defined as a pressure at an exit of the epoxidation reactor, and
  wherein the epoxidation reaction mixture is liquid under the epoxidation conditions.

9. The process of claim 1, wherein in (ii), a catalyst loading is from 0.05 to 1.25 h$^{-1}$, wherein the catalyst loading is defined as a ratio of a mass flow rate in kg/h of hydrogen peroxide comprised in the liquid feed stream prepared in (i)

divided by an amount in kg of catalyst comprising the titanium zeolite of structure MWW in the epoxidation reactor in (ii).

10. The process of claim 1, wherein in (ii), the catalyst comprising a titanium zeolite of framework structure MWW is present in the reactor as fixed-bed catalyst.

11. The process of claim 1, wherein a weight % of titanium in the titanium zeolite of framework structure MWW is from 0.1 to 5 weight-%, in (ii), calculated as elemental titanium, based on a total weight of the titanium zeolite of framework structure MWW.

12. The process of claim 1, wherein a weight-% zinc of the titanium zeolite of framework structure MWW, calculated as elemental zinc, is from 0.1 to 5 weight-%, based on a total weight of the titanium zeolite of framework structure MWW.

13. The process of claim 1, wherein the effluent stream removed in (iv) comprises
propylene oxide in amount of from 5 to 20 weight-%, based on a total weight of the effluent stream;
acetonitrile in amount of from 60 to 75 weight-%, based on the total weight of the effluent stream;
water in amount of from 10 to 25 weight-%, based on the total weight of the effluent stream; and
the dissolved potassium dihydrogenphosphate with a molar ratio of potassium dihydrogenphosphate relative to hydrogen peroxide comprised in the feed stream in a range of from $25\times10^{-6}:1$ to $1000\times10^{-6}:1$;
wherein at least 95 weight-% of the effluent stream removed in (iii) consists of propylene oxide, acetonitrile, water and potassium dihydrogen phosphate.

14. The process of claim 13, wherein the effluent stream removed in (iv) comprises molecular oxygen with a molar ratio of the molecular oxygen in the effluent stream removed in (iv) relative to hydrogen peroxide in the liquid feed stream provided in (i) in a range of from 0.05:100 to 2.5:100.

15. The process of claim 1, wherein the effluent stream removed in (iv) comprises propene and wherein the process further comprises
(iv) separating propene and oxygen from the effluent stream, thus obtaining a stream S01 enriched in propylene oxide, acetonitrile and water; and
(v) separating propylene oxide from S01, further obtaining a top stream comprising propylene oxide and being depleted of acetonitrile and water.

* * * * *